United States Patent
Maury et al.

(10) Patent No.: US 10,047,106 B2
(45) Date of Patent: Aug. 14, 2018

(54) LANTHANIDE COMPLEXES COMPRISING AT LEAST TWO BETAINE GROUPS, WHICH CAN BE USED AS LUMINESCENT MARKERS

(71) Applicants: ECOLE NORMALE SUPERIEURE DE LYON, Lyons (FR); UNIVERSITE CLAUDE BERNARD LYON I, Villeurbanne (FR); CENTRE NATIONAL DE LA RECHERCHE SCIENTIFIQUE, Paris (FR)

(72) Inventors: Olivier Maury, Brindas (FR); Chantal Andraud, Genas (FR); Virginie Placide, Lyons (FR); Delphine Pitrat, Villefontaine (FR)

(73) Assignees: ECOLE NORMALE SUPERIEURE DE LYON, Lyons (FR); UNIVERSITE CLAUDE BERNARD LYON I, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/775,244

(22) PCT Filed: Apr. 3, 2014

(86) PCT No.: PCT/FR2014/050813
§ 371 (c)(1),
(2) Date: Sep. 11, 2015

(87) PCT Pub. No.: WO2014/162105
PCT Pub. Date: Oct. 9, 2014

(65) Prior Publication Data
US 2016/0031910 A1 Feb. 4, 2016

(30) Foreign Application Priority Data
Apr. 4, 2013 (FR) .................................... 13 53037

(51) Int. Cl.
| | | |
|---|---|---|
| *C07F 5/00* | (2006.01) | |
| *C09K 9/02* | (2006.01) | |
| *G01N 33/533* | (2006.01) | |
| *G01N 33/58* | (2006.01) | |
| *C07D 401/14* | (2006.01) | |
| *C07D 213/79* | (2006.01) | |
| *C07D 401/04* | (2006.01) | |
| *C07D 255/02* | (2006.01) | |
| *C09K 11/06* | (2006.01) | |

(52) U.S. Cl.
CPC ............ *C07F 5/003* (2013.01); *C07D 213/79* (2013.01); *C07D 255/02* (2013.01); *C07D 401/04* (2013.01); *C07D 401/14* (2013.01); *C09K 9/02* (2013.01); *C09K 11/06* (2013.01); *G01N 33/533* (2013.01); *G01N 33/582* (2013.01); *C09K 2211/1007* (2013.01); *C09K 2211/1029* (2013.01); *C09K 2211/1059* (2013.01); *C09K 2211/182* (2013.01)

(58) Field of Classification Search
None
See application file for complete search history.

(56) References Cited

U.S. PATENT DOCUMENTS

| | | | |
|---|---|---|---|
| 4,761,481 | A | 8/1988 | Hale et al. |
| 4,859,777 | A | 8/1989 | Toner |
| 4,920,195 | A | 4/1990 | Kankare et al. |
| 4,927,923 | A | 5/1990 | Mathis et al. |
| 5,202,423 | A | 4/1993 | Kankare et al. |
| 5,216,134 | A | 6/1993 | Mukkala et al. |
| 5,324,825 | A | 6/1994 | Kankare et al. |
| 5,457,184 | A | 10/1995 | Lehn et al. |
| 5,622,821 | A | 4/1997 | Selvin et al. |
| 2003/0138876 | A1 | 7/2003 | Ponce et al. |
| 2014/0336373 | A1 | 11/2014 | Lamarque et al. |

FOREIGN PATENT DOCUMENTS

| | | |
|---|---|---|
| EP | 321353 A1 | 6/1989 |
| WO | 2001096877 A2 | 12/2001 |
| WO | 2008063721 A2 | 5/2008 |
| WO | 2009010580 A1 | 1/2009 |
| WO | 2013026790 A1 | 2/2013 |

OTHER PUBLICATIONS

IUPAC gold book, http://goldbook.iupac.org/html/B/B00637.html, accessed May 10, 2017.*
Butler. Dalton Transactions, 2014, 43, 5721-30.*
Placide. Tetrahedron Letetrs, 2014, 55, 1357-61, online Jan. 13, 2014.*
Periodic Table, http://www.chem.qmul.ac.uk/iupac/AtWt/table.html, accessed May 24, 2017.*
Anthony D'Aleo et al., :"Ytterbium-Based Bioprobes for Near-Infrared Two Photon Scanning Laser Microscopy Imaging", Angew. Chem. Int. Ed. 2012, 51, 6622-6625.
Zein El Abidine Chamas et al., :"Clicked dipicolinic antennae for lanthanide luminescent probes", Dalton Trans., 2010, 39, 7091-7097.
Svetlana V. Eliseeva et al., :"Lanthanide luminescence for functional materials and bio-sciences", Chem. Soc. Rev., 2010, 39, 189-227.
Pascal Kadjane, et al., :"Divergent Approach to a Large Variety of Versatile Luminescent Lanthanide Complexes", Inorg. Chem. 2009, 48, 4601-4603.
James W. Walton et al. :"Very bright europium complexes that stain cellular mitochondria", Chem. Commun., 2013, 49, 1600-1602.

(Continued)

*Primary Examiner* — Noble E Jarrell
(74) *Attorney, Agent, or Firm* — Ladas & Parry LLP; Malcolm J. MacDonald

(57) ABSTRACT

The present invention relates to luminescent lanthanide complexes including a chelating agent, formed with a macrocycle or a set of ligands, complexing a lanthanide ion Ln3+, wherein the chelating agent is substituted with at least two groups. The invention is most particularly applied to lanthanide complexes, the chelating agent of which is formed the with three ligands integrating a 2,6 pyridine-di (carboxylic acid) or is formed with a macrocycle having a 1,4,7 triazacyclononane structure.

21 Claims, 1 Drawing Sheet

(56) References Cited

OTHER PUBLICATIONS

Anthony D'Aleo et al., :"Sensitization of Eu(III) luminescence by donor-phenylethynyl-functionalized DTPA and DO3A macrocycles", C. R. Chimie 13 (2010) 681-690.

Adrien Bourdolle, et al., :"Modulating the Photophysical Properties of Azamacrocyclic Europium Complexes with Charge-Transfer Antenna Chromophores", Inorg. Chem. 2011, 50, 4987-4999.

Alexandre Picot et al. :"Long-Lived Two-Photon Excited Luminescence of Water-Soluble Europium Complex: Applications in Biological Imaging Using Two-Photon Scanning Microscopy", J. Am. Chem. Soc. 2008, 130, 1532-1533.

Martti Latva et al., :"Correlation between the lowest triplet state energy level of the ligand and lanthanide(III) luminescence quantum yield", Journal of Luminescence 75 (1997) 149-169.

Aline Nonat et al.: Structural and Photophysical Studies of Highly Stable Lanthanide Complexes of Tripodal 8-Hydroxyquinolinate Ligands Based on 1, 4, 7-Triazacyclononane, Inorg. Chem. 2009, 48, 4207-4218.

Craig P. Montgomery et al.:"Cell-Penetrating Metal Complex Optical Probes: Targeted and Responsive Systems Based on Lanthanide Luminescence", Accounts of Chemical Research, vol. 42, No. 7, Jul. 2009, 925-937.

Evan G. Moore et al. :"From Antenna to Assay: Lessons Learned in Lanthanide Luminescence", Accounts of Chemical Research, Apr. 2009, vol. 42, No. 4, 542-552.

Alexandre Picot et al. :Synthesis, structures, optical properties, and TD-DFT studies of donor-π-conjugated dipicolinic acid/ester/amide ligands, Tetrahedron 64 (2008) 399-411.

He Wei et al. :"Compact Zwitterion-Coated Iron Oxide Nanoparticles for Biological Applications", Nano Letters, vol. 12, No. 1, Jan. 11, 2012, pp. 22-25.

Eleonora Muro et al.:"Small and Stable Sulfobetaine Zwitterionic Quantum Dots for Functional Live-Cell Imaging", Journal of the American Chemical Society, vol. 132, No. 13, Apr. 7, 2010, pp. 4556-4557.

Chantal Andraud et al.: "Lanthanide Complexes for Nonlinear Optics: From Fundamental Aspects to Applications", European Journal of Inorganic Chemistry, vol. 2009, No. 29-30, Oct. 1, 2009, pp. 4357-4371.

International Search Report dated Jul. 31, 2014, corresponding to International Patent Application PCT/FR2014/050813.

* cited by examiner

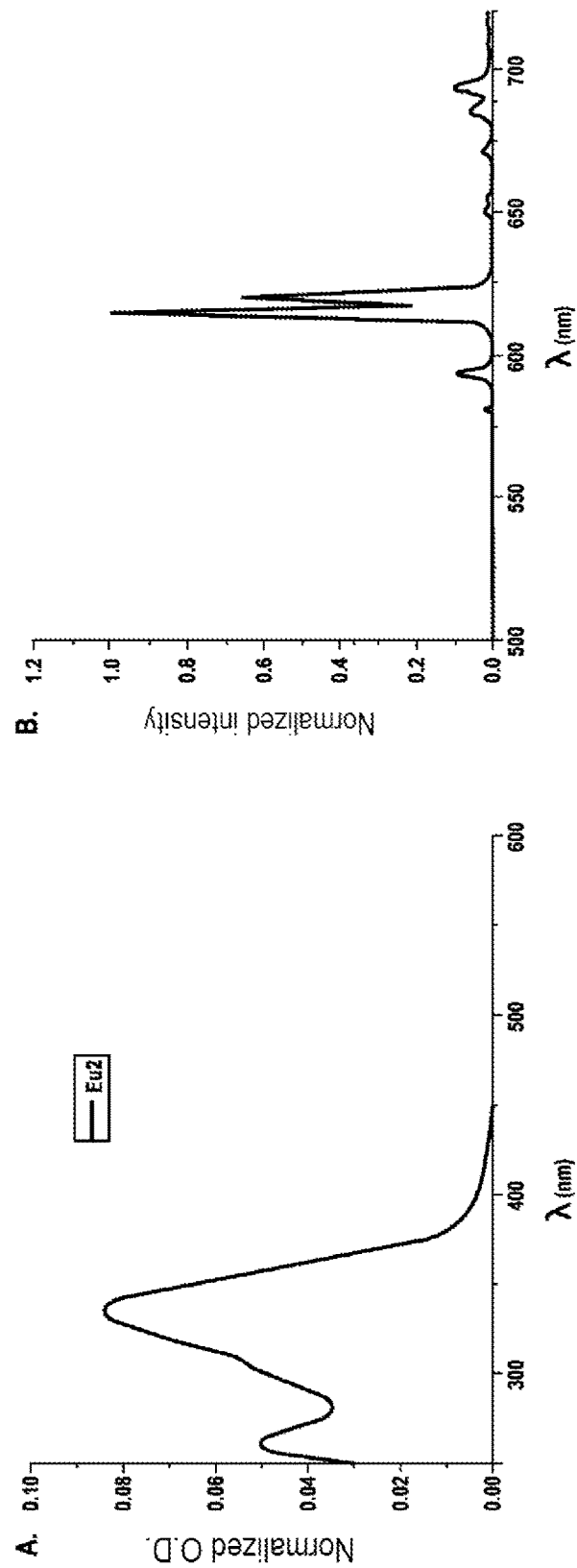

LANTHANIDE COMPLEXES COMPRISING AT LEAST TWO BETAINE GROUPS, WHICH CAN BE USED AS LUMINESCENT MARKERS

This application is a 371 of PCT/FR2014/050813, filed on Apr. 3, 2014, which claims priority to French Application No. 1353037, filed Apr. 4, 2013.

The present invention relates to the technical field of lanthanide complexes. In particular, the present invention relates to lanthanide complexes comprising at least two betaine groups on their organic portion, giving them interesting properties in terms of solubility in water and in biological media, and allows limitation, or even suppression of non-specific adhesion phenomena with biomolecules (proteins . . . ) or lipophilic portions of cells, notably allowing their use in biological applications.

Certain lanthanide complexes have remarkable spectroscopic properties (fine emission bands characteristic of a given metal and with a long lifetime) and are, consequently, compounds with a very strong potential for applications in biological imaging (S. V. Eliseeva, J.-C. G. Bünzli, Chem. Soc. Rev. 2010, 39, 189). These luminescent compounds may be used alone for applications in imaging by mono- or bi-photon fluorescence microscopy, or else in conjunction with a suitable fluorophore for carrying out FRET (Förster/Fluorescence Resonant Energy Transfer) experiments. In the latter case, the lanthanide complexes are generally in the form of a conjugate complex with a biomolecule. Both of these techniques may optionally be resolved in time, by the long lifetime of lanthanides, which is an important advantage for improving detection while getting rid of parasitic fluorescence signals with a short lifetime (C. P. Montgomery B. S. Murray, E. J. New, R. Pal, D. Parker, Acc. Chem. Res. 2009, 42, 925. E. G. Moore, A. P. S. Samuel, K. N. Raymond, Acc. Chem. Res. 2009, 42, 542.). Many other luminescent lanthanide compounds have been described in the literature for such applications (M. Latva, H. Takalo, V.-M. Mukkala, C. Matachescu, J. C. Rodríguez-Ubis, J. Kankare, J. Lumin., 1997 75 149-169; A. Picot, A. D'Aléo, P. L. Baldeck, A. Grichine, A. Duperray, C. Andraud, O. Maury, J. Am. Chem. Soc. 2008, 130, 1532) and some of them are marketed as derivatives of DTPA (diethylene triamine penta acid, U.S. Pat. No. 5,622,821), compounds based on pyridine or poly-pyridine (U.S. Pat. No. 4,920,195; U.S. Pat. No. 4,761,481; U.S. Pat. No. 5,216,134; U.S. Pat. No. 4,859,777; U.S. Pat. No. 5,202,423; U.S. Pat. No. 5,324,825), or further macrocyclic cryptates (EP 0 180 492; EP 0 321353; EP 0 601 113; WO 2001/96877; WO 2008/063721).

In the past, lanthanide complexes had a simple structure with not very much carbon, were generally charged, and consequently were therefore soluble in water. With the developments during these recent years, functionalized complexes were developed for optimizing their spectroscopic properties, displacing their absorption towards visible light and optimizing their bi-photon absorption. Increasingly, functional antennas generally conjugate and/or aromatic including a large number of carbons are introduced, which leads to lipophilic compounds, therefore not soluble in water (C. Andraud, O. Maury Eur. J. Inorg. Chem. 2009, 4357-4371).

In order to increase hydrosolubilization of lanthanide complexes, different approaches were developed. One approach consists of introducing polyethylene glycol (PEG) groups as hydrosolubilizing groups. A. Picot, A. D'Aléo, P. L. Baldeck, A. Grichine, A. Duperray, C. Andraud and O. Maury, in J. Am. Chem. Soc., 2008, 130, 1532-153.3 used this approach in the case of lanthanide complexes for which the complexation is ensured by three ligands integrating a 2,6-pyridine-carboxylic diacid. The introduction of PEG groups is also contemplated in C. R. Chim., 2010, 13, 681-690, Inorg. Chem., 2011, 50, 4987-4999 and Angew. Chem. In. Ed. 2012, 51, 6622-6625.

Patent application WO 2013/011236, relating to strongly luminescent lanthanide compounds, for which certain are based on a 1,4,7-triazacyclononane ring (TACN) substituted with chromophores based on conjugate pyridine, also use PEG groups. The described complexes are very stable in water and the presence of PEG groups ensures their good solubility.

These functional macrocyclic ligands notably lead to the formation of europium complexes which have very high brightness at 337 nm (the brightness is defined by the product of the quantum yield by the absorption at the wavelength of interest, here 337 nm), 337 nm corresponding to the excitation wavelength of the nitrogen laser used for commercial applications (J. W. Walton, A. Bourdolle, S. J. Butler, M. Soulier, M. Delbianco, B. K. McMahon, R. Pal, H. Puschmann, J. M. Zwier, L. Lamarque, O. Maury, C. Andraud and D. Parker Chem. Commun. 2013, 49, 1600-1602).

These compounds may also be provided with a reactive function, so as to be optionally conjugate by a covalent bond to a molecule of interest, such as a biomolecule. In this case, the compounds have the end purpose of being bound covalently to a biomolecule, with view to conducting FRET experiments (HTRF® applications marketed by CISBIO BIOASSAYS).

However, these compounds have two major drawbacks:

1) Within the scope of their research work, the inventors observed that these complexes are adsorbed in a non-specific way on biomolecules, which complicates the preparation of conjugate biomolecules. This phenomenon is also found in imaging experiments by mono- or bi-photon microscopy conducted on set cells. In this case, specific accumulation of these compounds in the lipophilic membranes and/or organelles is ascertained. The inventors of the present invention associated this drawback with the presence of PEG groups.

2) Further, these compounds are prepared via a not very polyvalent, long and with modest efficiency convergent synthesis route.

Other solutions propose solubilization of the lanthanide complexes by introducing anionic charged groups. In Inorg. Chem. 2009, 48(9), 4207-4218, hydrosolubilization is ensured by —$SO_3$ groups, whereas in Inorg. Chem., 2009, 48, 4601-4603, the hydrosolubilization is ensured by —$CO_3$ groups. In these examples, the introduction of anionic groups gives the possibility of ensuring good hydrosolubilization, the problem of the non-specific adsorption is not tackled and no example describes their behavior in the presence of bioconjugates.

The present invention proposes provision of novel fluorescent lanthanide complexes which have satisfactory solubility in water and therefore in physiological and biological media, but they do not have the drawback of the previous solutions, and notably of those using PEG groups, for which the inventors ascertained a tendency to adhere to biomolecules, to cell membranes and more generally to hydrophobic portions present in a large number in biomolecules and biological media.

In this context, the invention relates to luminescent lanthanide complexes including a chelating agent, formed with a macrocycle or a set of ligands, complexing a lanthanide ion $Ln^{3+}$, wherein the chelating agent is substituted with at least two betaine groups.

As an example of a lanthanide ion $Ln^{3+}$, mention may be made of $Eu^{3+}$, $Sm^{3+}$, $Tb^{3+}$ or $Dy^{3+}$.

Within the scope of the invention, the solubilization of lanthanide complexes in an aqueous medium is ensured by zwitterionic hydrosolubilizing groups of the betaine type.

The present invention proposes a functionalization of lanthanide complexes with two betaine groups or more. This functionalization gives the possibility of solubilizing the lanthanide complexes in water and biological media and makes it possible to avoid non-specific adhesion phenomena with biomolecules and organelles. This functionalization may be applied to all types of lanthanide complexes. Further, within the scope of the invention, it was demonstrated that the presence of betaine groups did not affect the luminescence properties of the complexes.

Admittedly, betaines, in a very large number, had already been used for functionalizing nano-objects such as paramagnetic nanoparticles or quantum dots (H. Wei, N. Insin, J. Lee, H.-S. Han, J. M. Cordero, Wenhao Liu, M. G. Bawendi Nano Lett. 2012, 12, 22-25; E. Muro, T. Pons, N. Lequeux, A. Fragola, N. Sanson, Z. Lenkei, B. Dubertret J. Am. Chem. Soc 2010, 132, 4556-4557). However, in this type of polyfunctional nano-objects, it is impossible to determine whether the limitation of the non-specific adhesion phenomena observed might stem from the actual nature of the betaine group or from the simultaneous presence of a very large number of these functions (a so-called multivalence phenomenon). Thus, according to present knowledge, it was totally impossible to predict the behavior of small molecules, such as lanthanide complexes, functionalized with betaine groups. In the literature, betaine groups have also been introduced on organic chromophores (cyanines, bodipy) for making them soluble in water, but nothing is described as regards a possible property of non-adhesion. The non-adhesion property obtained for molecular compounds, like in the case within the scope of the invention, was therefore by no means predictable.

A betaine group is defined as a zwitterionic group wherein the atom bearing the positive charge does not bear any hydrogen atom and is not adjacent to the atom bearing the negative charge. Within the scope of the invention, by betaine is for example meant the zwitterionic groups associating an ammonium cation or aromatic iminium, generally pyridinium, imidazolium, and an anionic group of the sulfonate, phosphonate or carboxylate type, preferably sulfonate. The cation and the anion are spaced apart by at least one $CH_2$ ring member, and preferably by a bivalent alkyl chain (also-called alkylene) comprising from 1 to 4, or even from 1 to 6 carbon atoms. As an example of a betaine group, mention may be made of the groups of formula:

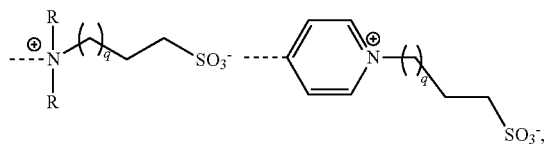

with R representing an alkyl group from 1 to 6 carbon atoms, and preferably a methyl or ethyl, and q being equal to 1, 2, 3, 4, 5 or 6, and preferably equal to 1 or 2. The group $-N(CH_3)_2{}^+-(CH_2)_3-SO_3{}^-$ is preferred.

Advantageously, the lanthanide complexes according to the invention include a chelating agent substituted with at most 12 betaine groups, for example 2, 3, 4, 5, 6, 7, 8, 9, 10 or 11 betaine groups.

Moreover, the complexes according to the invention may also be provided with a reactive function, in order to allow their conjugation through a covalent bond to a molecule of interest, such as a biomolecule. By reactive function, is meant a function allowing covalent grafting on a reactive function present on a biomolecule (amine, alcohol, thiol, carboxylic acid, unsaturated functions . . . ). The various functions allowing such bioconjugation are well known to one skilled in the art and for example are described in Bioconjugate Techniques, G. T. Hermanson, Academic Press, 1996, 137-166. Preferably, this reactive function will be an amine function, an activated ester, an azido group. In particular, the lanthanide complexes according to the invention will include one chelating agent substituted with at least one, and in particular a single one, reactive function allowing its coupling through a covalent bond with a biomolecule, said reactive function being preferably selected among $-COOH$, $-NH_2$, an acrylamide, an activated amine, an activated ester, an aldehyde, an alkyl halide, an anhydride, an aniline, an azide, an aziridine, a carboxylic acid, a diazoalkane, a haloacetamide, a halotriazine, a hydrazine, an imido ester, an isocyanate, an isothiocyanate, a maleimide, a sulfonyl halide, a thiol, a ketone, an amine, an acid halide, a hydroxysuccinimidyl ester, a succinimidyl ester, a hydroxysulfosuccinimidyl ester, an azidonitrophenyl, an azidophenyl, a 3-(2-pyridyl-dithio)-propionamide, a glyoxal, a triazine, an acetylenic group, and groups of formula:

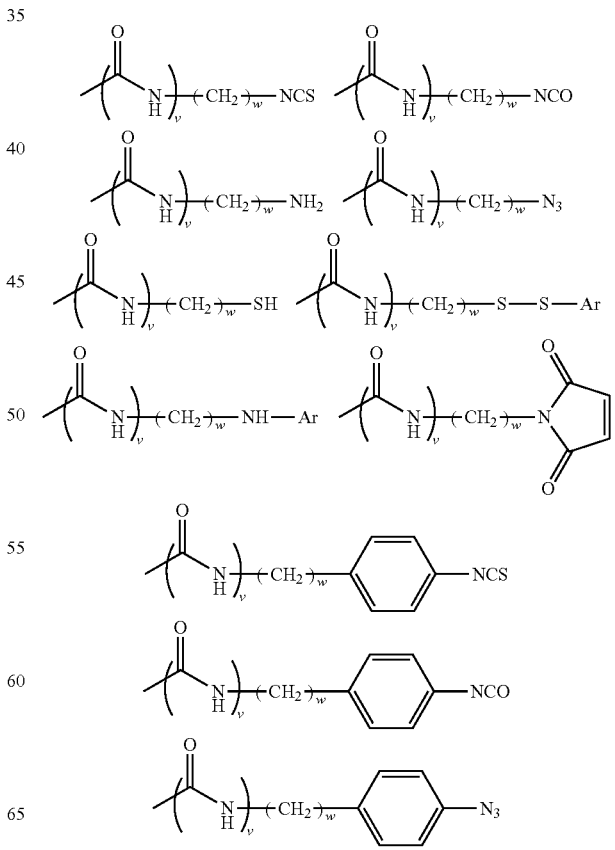

-continued

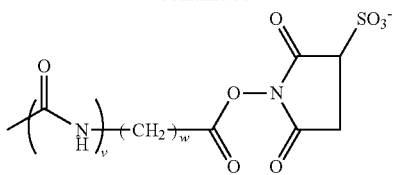

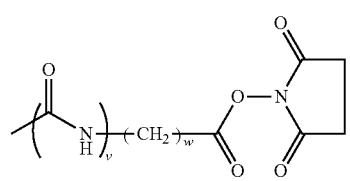

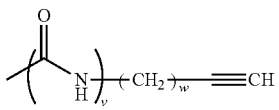

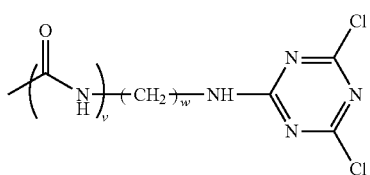

wherein w is an integer belonging to the range from 0 to 8 and v is equal to 0 or 1, and Ar is a heterocycle with 5 or 6 members, either saturated or unsaturated, comprising from 1 to 3 heteroatoms, optionally substituted with a halogen atom;

the reactive functions selected from —COOH, —NH$_2$, succinimidyl esters, haloacetamides, azides, hydrazines, isocyanates and maleimides being preferred.

By biomolecules, are meant molecules of biological interest for which it may be advantageous to mark them by means of a luminescent complex, for example, proteins, peptides, antibodies, antigens, DNA strands, biotin, streptavidin. Proteins are biomolecules which will most often be bound to the complexes according to the invention.

Examples of lanthanide complexes according to the invention include a chelating agent formed with three ligands integrating a 2,6-pyridine-dicarboxylic acid group or formed with a macrocycle with a 1,4,7-triazacyclononane structure.

In particular, the invention relates to lanthanide complexes selected from the lanthanide complexes of formula (IV):

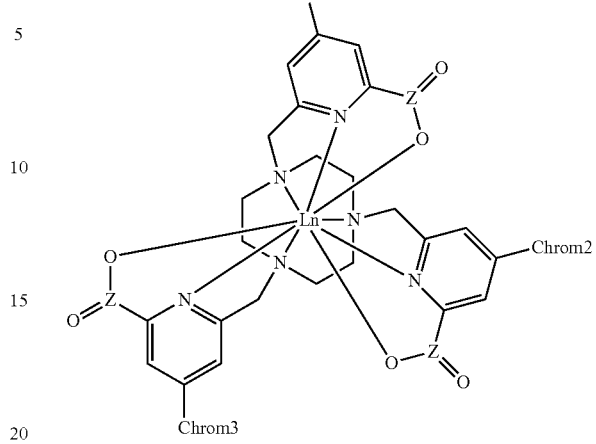

wherein:
Ln is a lanthanide, notably Eu, Sm, Tb or Dy,
Z represents —C— or —PR$_3$—,
R$_3$ represents a phenyl, benzyl, methyl, ethyl, propyl, n-butyl, sec-butyl, iso-butyl or tert-butyl group and preferably a phenyl or methyl group,
Chrom1, Chrom2 and Chrom3, either identical or different, are selected from the groups:

wherein:
L$_1$ represents a direct bond, —C=C— or —C≡C—,
Ar$_1$ represents an aromatic group selected from phenyl, thiophenyl, furanyl, pyrrolyl, imidazolyl or triazolyl groups, substituted with s groups R$_0$ either identical or different,
s is equal to 1, 2 or 3, and
R$_0$ is selected among alkyl groups comprising from 1 to 10, and preferably from 1 to 6 carbon atoms; the alkyl groups comprising from 1 to 10 carbon atoms bearing at least one betaine function and/or a reactive function; and electron donor groups, notably O donors, S donors, NHCO donors, SCO donors, NHCS donors, and SCS donors, said electron donor groups may either bear or not one or several betaine groups, and/or a reactive function, it being understood that when all the groups Ar1 represent a phenyl group, at least one of these phenyl groups, preferably two or even three of these groups, is (are) substituted with at least one group R$_0$ including an electron donor group;
characterized in that at least two of the Chrom1, Chrom2 and Chrom3 groups are substituted with at least one group R$_0$ bearing at least one betaine group.

Preferably, in the complexes of formula (IV), Chrom1, Chrom2 and Chrom3 are defined as follows:
a. either Chrom1, Chrom2 and Chrom3, either identical or different, are selected from the groups:

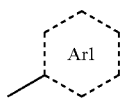

with Ar1 as defined for the complexes of formula (IV), (which corresponds to the case when $L_1$ represents a direct or covalent bond), b. or Chrom1, Chrom2 and Chrom3, either identical or different, are selected from groups:

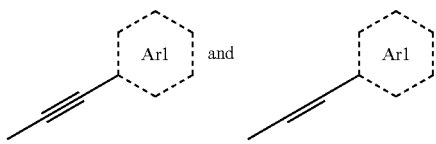

with Ar1 which represents a phenyl, thiophenyl, furanyl, pyrrolyl or imidazolyl group substituted with s groups $R_0$ either identical or different, s and $R_0$ being as defined for the complexes of formula (IV).

In the complexes of formula (IV) according to the invention, the $R_0$ substituents, either identical or different, are, for example, selected among:

-$L_2$-Alk, -$L_2$-$L_3$-$Q_1$ and -$L_2$-$L_3$-$Q_2$;

the NHCO donor groups are selected from: —NHCO(OAlk), —NHCO(NHAlk), —NHCO(NAlk1Alk2), —NHCO(SAlk), the SCO donor groups are selected from: —SCO(OAlk), —SCO(NHAlk), —SCO(NAlk1Alk2), —SCO(SAlk), the NHCS donor groups are selected from: —NHCS(OAlk), —NHCS(NHAlk), —NHCS(NAlk1Alk2), and the SCS donor groups are selected from: —SCS(OAlk), —SCS(NHAlk), —SCS(NAlk1Alk2), —SCS(SAlk), Alk, Alk1 and Alk2, either identical or different, are alkyl groups comprising from 1 to 10 carbon atoms, optionally substituted with at least one betaine group, $Q_1$ represents a betaine group or a branched group bearing at least two betaine groups, $L_2$ is a direct bond, —O—, —S—, —NHCO—, —SCO—, —NHCS— or —SCS—

$L_3$ is a bond arm, and $Q_2$ is a reactive group which may allow the covalent bond with a molecule of interest to be marked, it being understood that at least two of the present $R_0$ substituents bear at least one betaine group, so that at least two of the groups Chrom1, Chrom2 and Chrom3 are substituted with at least one $R_0$ group bearing at least one betaine group.

As an example of a branched group bearing at least two betaine groups, mention may be made of the groups of the following formula:

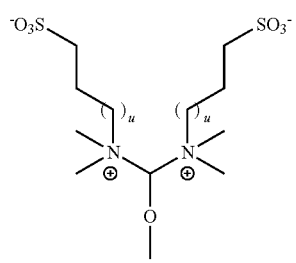

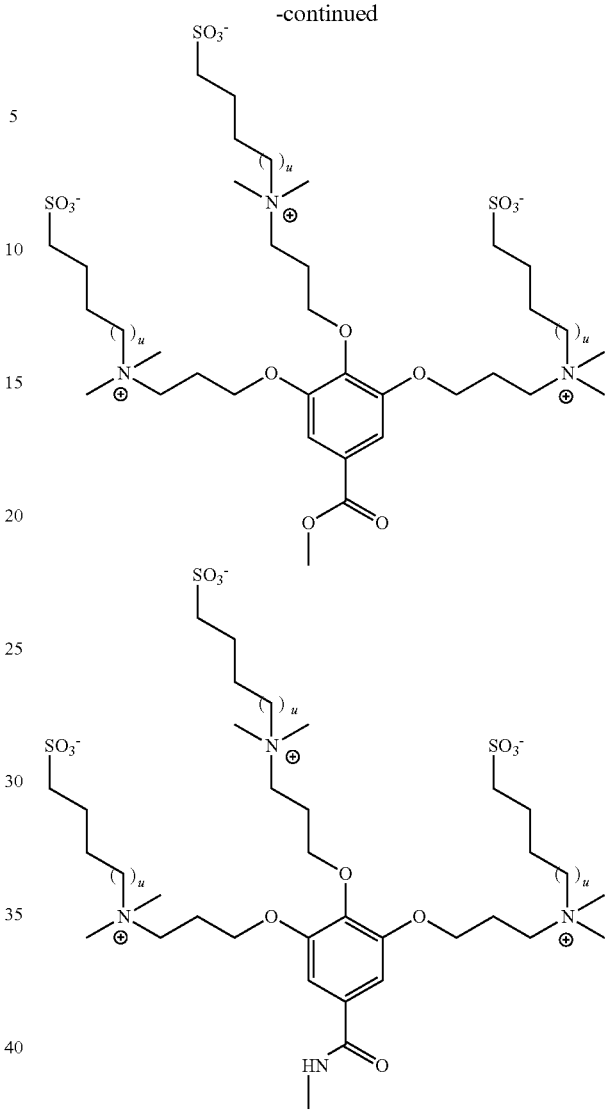

with u which is equal to 1, 2, 3, 4, 5 or 6.

In the complexes of formula (IV) according to the invention, it is possible that Chrom1=Chrom2=Chrom3 or preferably that Chrom1=Chrom2 and are substituted with at least one group $R_0$ bearing at least one betaine group and that Chrom3 is substituted with at least one group $R_0$ bearing a function -$L_2$-$L_3$-$Q_2$, as defined earlier, with preferably $Q_2$ which represents a group selected from —COOH, —$NH_2$, an acrylamide, an activated amine, an activated ester, an aldehyde, an alkyl halide, an anhydride, an aniline, an azide, an aziridine, a carboxylic acid, a diazoalkane, a haloacetamide, a halotriazine, a hydrazine, an imido ester, an isocyanate, an isothiocyanate, a maleimide, a sulfonyl halide, a thiol, a ketone, an amine, an acid halide, a hydroxysuccinimidyl ester, a succinimidyl ester, a hydroxysulfosuccinimidyl ester, an azidonitrophenyl, an azidophenyl, a 3-(2-pyridyldithio)-propionamide, a glyoxal, a triazine, an acetylenic group, and the groups of formula:

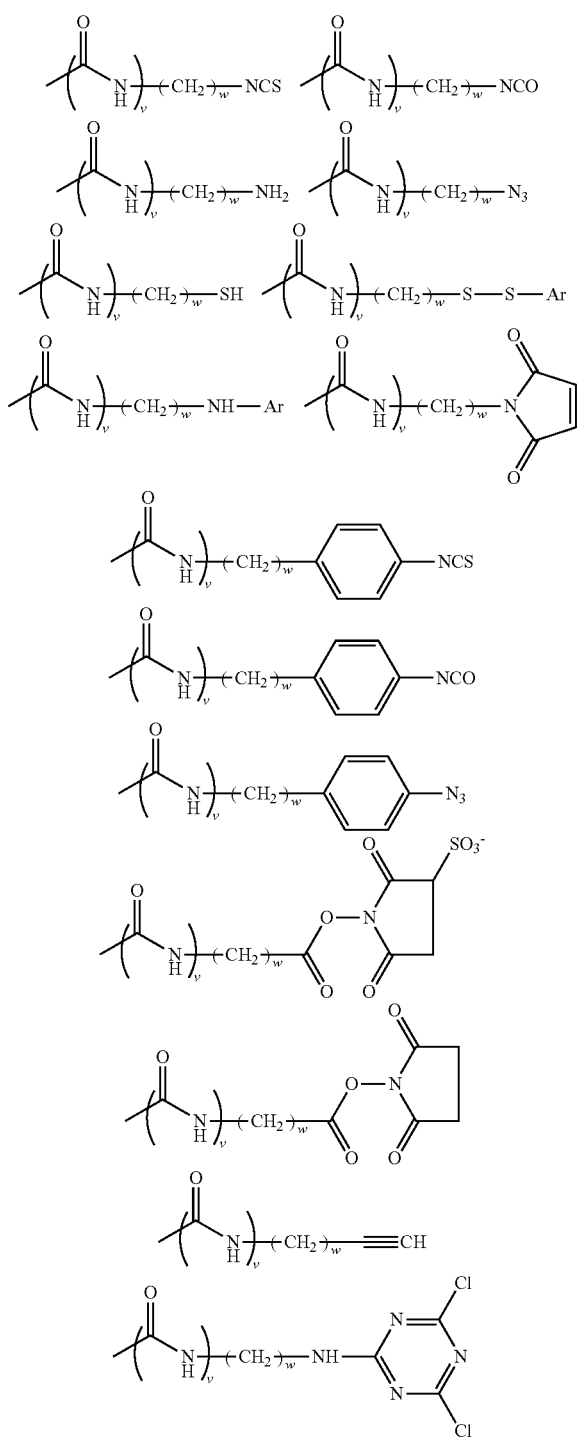

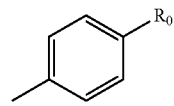

a phenyl group, substituted with s $R_0$ groups either identical or different, with s and $R_0$ being as defined for the complexes of formula (IV), are examples of complexes according to the invention.

The complexes of formula (IV) according to the invention wherein s is equal to 1 for all the Ar1 groups are simpler to synthesize and will be preferred.

As an example of complexes of formula (IV) according to the invention, mention may be made of those for which all the Ar1 groups, either identical or different, represent a phenyl group selected from the groups:

with $R_0$ as defined for the complexes of formula (IV).

The invention also relates to the lanthanide complexes of formula (III):

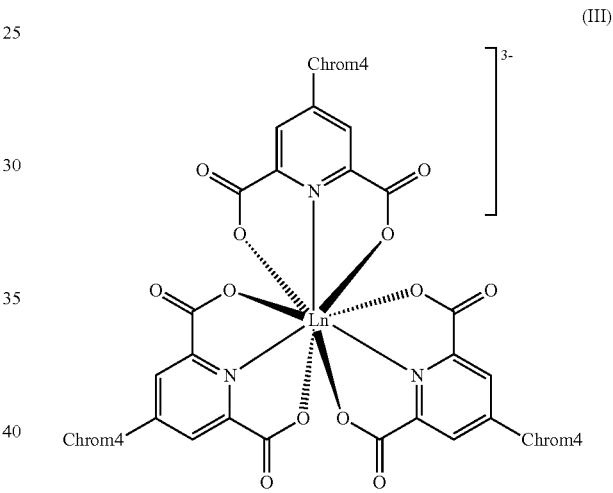

(III)

wherein:
Ln is a lanthanide, notably Eu, Sm, Tb or Dy,
Chrom4 is selected from the groups:

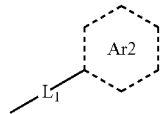

wherein:
$L_1$ represents a direct bond, —C═C— or —C≡C—,
Ar2 represents an aromatic group selected from phenyl, thiophenyl, furanyl, pyrrolyl, imidazolyl or triazolyl groups, said groups Ar2 being substituted with s groups $R_1$ either identical or different,
s is equal to 1, 2 or 3, and
$R_1$ is selected among alkyl groups comprising from 1 to 10 carbon atoms bearings at least one betaine group; and the electron donor groups, notably O donors, S donors, NHCO donors, SCO donors, NHCS donors, and SCS donors, said electron donors bearing one or several betaine groups, wherein w is an integer belonging to the range from 0 to 8 and v is equal to 0 or 1, and Ar is a heterocycle with 5 or 6 members, either saturated or unsaturated, comprising from 1 to 3 heteroatoms, optionally substituted with a halogen atom;
$Q_2$ is preferably selected from —COOH, —NH₂, succinimidyl esters, haloacetamides, hydrazines, isocyanates and maleimides being preferred.

The complexes of formula (IV) according to the invention, wherein $L_1$ represents a direct bond or —C≡C—, and the groups Ar1, either identical or different, each represent it being understood that when the group Ar2 represents a phenyl group, it is substituted with at least one group $R_1$ including an electron donor group.

In the complexes of formula (III) according to the invention, Ar2 is for example, selected
c. either from the groups:

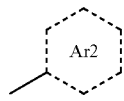

with Ar2 as defined for the complexes of formula (III) (which corresponds to the case when $L_1$ represents a direct or covalent bond),
d. or from the groups:

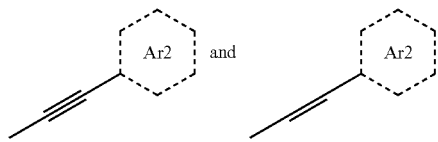

with Ar2 which represents a phenyl, thiophenyl, furanyl, pyrrolyl or imidazolyl group substituted with s groups $R_1$ either identical or different, s and $R_1$ being as defined for the complexes of formula (III).

Preferably, in the complexes of formula (III) according to the invention, the substituents $R_1$, either identical or different, are selected from:

$L_2$-Alk, -$L_2$-$L_3$-$Q_1$;
the NHCO donor groups are selected from: —NHCO(OAlk), —NHCO(NHAlk), —NHCO(NAlk1Alk2), —NHCO(SAlk),
the SCO donor groups are selected from: —SCO(OAlk), —SCO(NHAlk), —SCO(NAlk1Alk2), —SCO(SAlk),
the NHCS donor groups are selected from: —NHCS(OAlk), —NHCS(NHAlk), —NHCS(NAlk1Alk2), and
the SCS donor groups are selected from: —SCS(OAlk), —SCS(NHAlk), —SCS(NAlk1Alk2), —SCS(SAlk),
Alk, Alk1 and Alk2, either identical or different, are alkyl groups comprising from 1 to 10 carbon atoms, substituted with at least one betaine group,
$Q_1$ represents a betaine group or a branched group bearing at least two betaine groups,
$L_2$ is a direct bond, —O—, —S—, —NHCO—, —SCO—, —NHCS— or —SCS—,
$L_3$ is a bond arm.

In the complexes of formula (III) and (IV) according to the invention, $L_3$ preferably represents a covalent bond, an alkylene group from 1 to 12 carbon atoms, optionally comprising one or several double or triple bonds; a cycloalkylene group from 5 to 8 carbon atoms, an arylene group from 6 to 14 carbon atoms; or a sequence of one or several alkylene groups from 1 to 12 carbon atoms, cycloalkylene group from 5 to 8 carbon atoms and/or arylene group from 6 to 14 carbon atoms; said alkylene, cycloalkylene or arylene groups may comprise or not one or several heteroatoms such as oxygen, nitrogen, sulphur, phosphorous or one or several carbamoyle or carboxamido groups and/or which may be non-substituted or substituted with one or several alkyl groups from 1 to 8 carbon atoms, aryl from 6 to 14 carbon atoms, sulfonate or oxo group; the following bond arms being preferred:

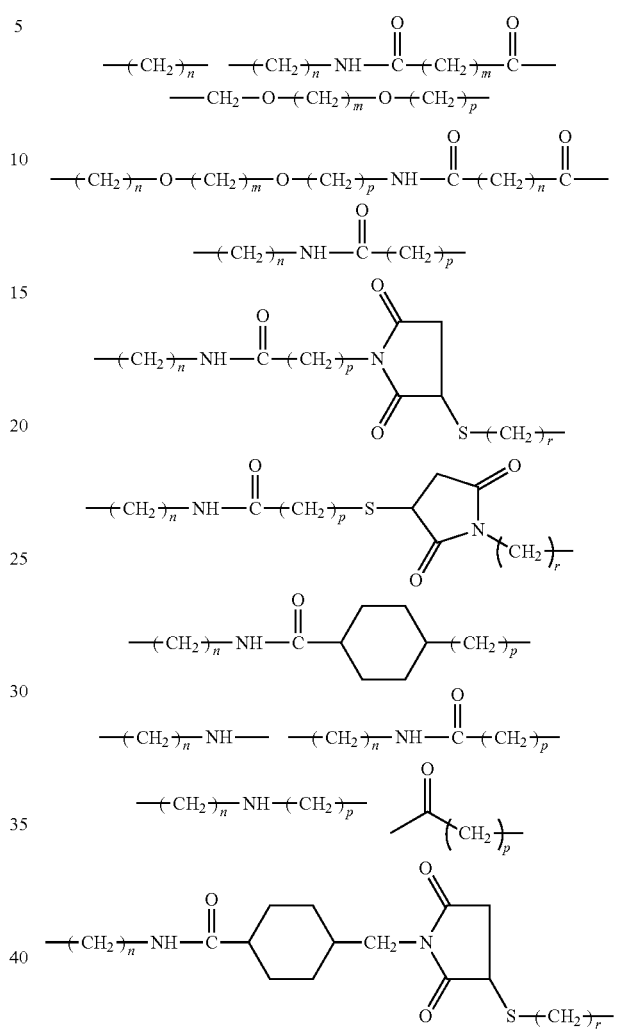

n is equal to 1, 2, 3, 4, 5 or 6,
m, p and r, either identical or different, are equal to 1, 2 or 3.

When $L_2$ and $L_3$ each represent a direct bond (equally called a covalent bond), -$L_2$-$L_3$-$Q_1$, corresponds to -$Q_1$ and -$L_2$-$L_3$-$Q_2$ to -$Q_2$ In the complexes of formula (IV) and (III) defined within the scope of the invention, if $Ln^{3+}=Eu^{3+}$ or $Snn^{3+}$, in this case, according to a preferred embodiment $L_1$ will be selected, which represents —C≡C—, which leads to suitable luminescence properties.

In the complexes of formula (IV) and (III) defined within the scope of the invention, if $Ln^{3+}=Eu^{3+}$, $Sm^{3+}$, $Tb^{3+}$ or $Dy^{3+}$ (and, in particular $Tb^{3+}$ or $Dy^{3+}$), according to a preferred embodiment $L_1$ will be selected, which represents a direct bond (also-called a covalent bond).

In the complexes of formula (IV) and (III) defined within the scope of the invention, the present betaine groups are for example zwitterionic groups associating an ammonium cation, or aromatic iminium, generally pyridinium, imidazolium, and an anionic group of the sulfonate, phosphonate or carboxylate type, preferably sulfonate, the cation and the anion being spaced apart by at least one ring member CH$_2$, and preferably by a bivalent alkyl chain (also-called alkylene) comprising from 1 to 4, or even from 1 to 6, carbon atoms. Preferably, the betaine groups present in the complexes of formula (IV) and (III) are selected from:

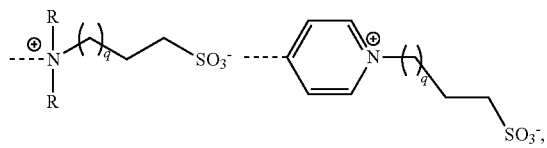

with R which represents an alkyl group from 1 to 6 carbon atoms, and preferably a methyl or ethyl, and q which is equal to 1, 2, 3, 4, 5 or 6, and preferably which is equal to 1 or 2, the group —N(CH$_3$)$_2$$^+$—(CH$_2$)$_3$—SO$_3$$^-$ being preferred.

The object of the invention is also:
chelating agents of formula (II):

formula (II)

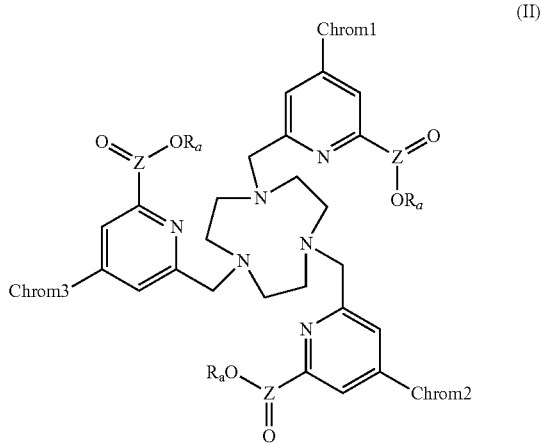

with Ra which is protective group of acid functions such as an alkyl, of the methyl type, and Z, Chrom1, Chrom2 and Chrom3, either identical or different, which are as defined for the compounds of formula (IV); and
the ligands of formula (I):

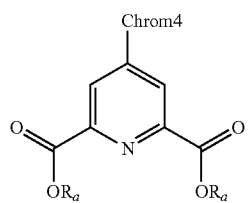

with Ra which is a protective group of acid functions such as an alkyl, of the methyl type, and Chrom4 which is as defined for the compounds of formula (III).

Within the scope of the invention, by «alkyl» group, unless specified otherwise, is meant a linear or branched saturated hydrocarbon chain. As an example of an alkyl group comprising from 1 to 6 carbon atoms, mention may notably be made of methyl, ethyl, n-propyl, iso-propyl, n-butyl, tert-butyl, sec-butyl, n-pentyl, n-hexyl groups.

By «cycloalkyl», is meant a saturated or unsaturated hydrocarbon group consisting of at least one ring, optionally a bridged ring. As an example, mention may be made of cyclopropyl, cyclobutyl, cyclopentyl, cyclohexyl, cycloheptyl, adamantyl and cyclohexene groups.

By «aryl» groups, are meant mono-, bi- or poly-cyclic groups, preferably including from 6 to 12 carbon atoms, comprising at least one aromatic group, for example a phenyl, cinnamyl or naphthyl group, as well as heteroaryl groups. By heteroaryl group is meant a mono-, bi- or poly-cyclic carbocycle, preferably including from 6 to 12 members, and comprising at least one aromatic group and at least one heteroatom selected from oxygen, nitrogen or sulphur atom, integrated within the carbocycle. As an example of a heteroaryl group, mention may be made of 2-, 3- or 4-pyridinyl, 2- or 3-furoyl, 2- or 3-thiophenyl, pyrrolyl, imidazolyl, pyrazolyl, thiazolyl, oxazolyl, isoxazolyl, pyridinyl, pyrazinyl, pyrimidinyl, tetrazolyl, thiadiazolyl, oxadiazolyl, triazolyl, pyridazinyl, indolyl groups. Phenyl and 1,2,3-triazole are particularly preferred aryl groups.

Advantageously, the complexes according to the invention are luminescent. The luminescence corresponds to a light emission consecutive to a supply of energy, in particular a supply of light. This energy supply causes atoms or molecules to pass into an «excited» state located at a higher energy than that which they had in their normal state, a so-called «fundamental» state. It is when they return to their fundamental state that they may emit light. Generally, lanthanide complexes are sensitized by an antenna effect and the nature of the organic antenna controls the absorption of light and allows optimization of the luminescence of the lanthanide (S. V. Eliseeva, J.-C. G. Bünzli, Chem. Soc. Rev. 2010, 39, 189).

Within the scope of the invention, the antenna advantageously consists of a pyridine derivative functionalized in position 4 by a conjugate system called a chromophore and notably defined under the names of Chrom1, Chrom2, Chrom3 and Chrom4 in the preferred complexes. This chromophore optionally consists of a conjugate spacer selected from double or triple carbon-carbon bonds, which advantageously corresponds to the —C≡C— bond, and of an aryl or heteroaryl group substituted with 1, 2 or 3 groups, so that at least 2 betaine groups are present on the final complex. The antennas in which the aryl or heteroaryl group is directly bound to pyridine will be preferred for sensitizing europium, samarium, terbium and dysprosium complexes, while the antennas including a conjugate spacer will be preferred for the europium and samarium complexes.

More particularly, the invention is applied to chelating ligands described in their protected form according to formula (I) or to chelating macrocycles described in their protected form according to formula (II) and to their corresponding lanthanide complexes according to formulae (III) and (IV).

According to formula (III) is described the family of lanthanide complexes from the coordination of 3 identical chelating ligands of formulae (I) after de-protection and release of the acid functions.

According to formula (IV), is described the family of lanthanide complexes from the coordination of a macrocyclic ligand of formula (II) after de-protection and release of the acid functions.

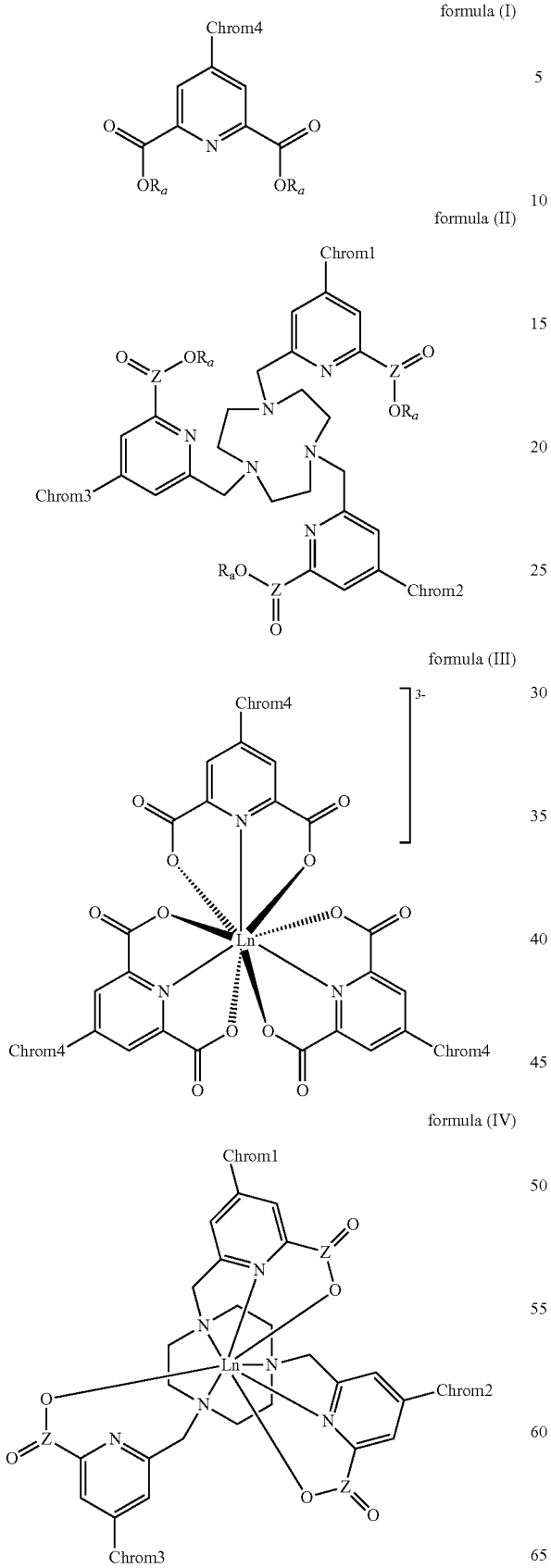

formula (I)

formula (II)

formula (III)

formula (IV)

As an example of a sub-structure of the complexes of formula (III) and (IV) as exemplified in the examples, mention may be made of:

a) the complexes (IVa)

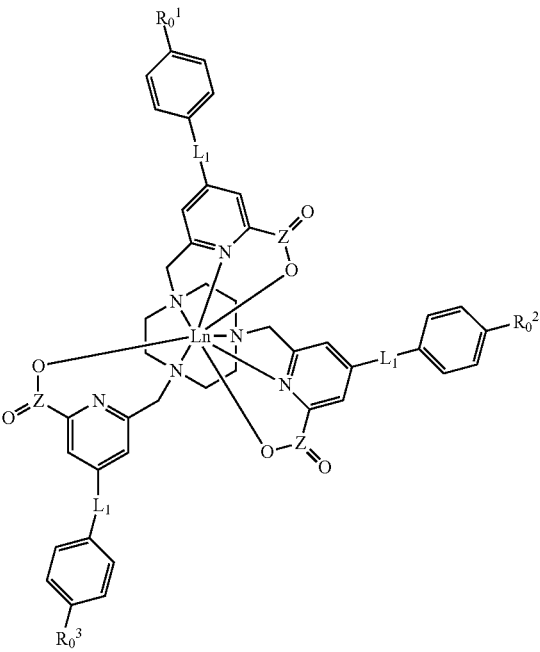

(IVa)

with $L_1$ as defined within the scope of the invention and which preferably represents —C≡C—, Z as defined for the complexes of formula (IV) and which preferably represents a carbon atom and $R_0^1$, $R_0^2$ and $R_0^3$, either identical or different, which represent a group $R_0$ as defined for the complexes of formula (IV), at least two of the groups $R_0^1$, $R_0^2$ and $R_0^3$ being substituted with at least one betaine group, b) the complexes (IIIa)

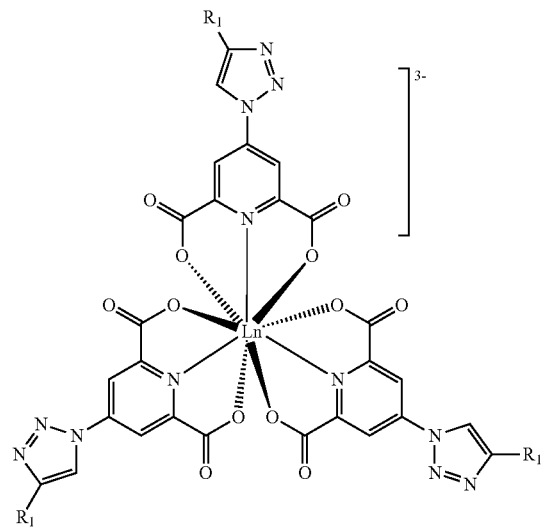

(IIIa)

with $R_1$ as defined for the complexes of formula (III).

The preparation of the complexes according to the invention applies standard techniques and reactions known to one skilled in the art. They may notably be obtained according to methods similar to those used in the examples.

The starting reagents are commercially available or easily accessible. The compounds of formulae (I) and (II) are therefore chemically accessible in a relatively standard way, and may be obtained at a reasonable preparation cost.

The functional groups optionally present in the compounds of formula (I) and (II) and in the reaction intermediates may be protected during the synthesis, either permanently or temporarily, with protective groups which ensure a one-one synthesis of the expected compounds. The protection and de-protection reactions are carried out according to techniques well known to one skilled in the art. By temporary protective group of amines, alcohols or carboxylic acids, are meant the protective groups like those described in Protective Groups in Organic Synthesis, Greene T. W. and Wuts P. G. M., ed. John Wiley and Sons, 2006 and in Protecting Groups, Kocienski P. J., 1994, Georg Thieme Verlag.

The complexation reactions are generally conducted with a salt of the desired lanthanide notably a chloride, a nitrate or a triflate in a dissociating solvent, notably an alcohol and preferably methanol or acetonitrile, or further in a mixture of solvents, in the presence of a base, generally a carbonate, at a temperature comprised between 25 and 80° C., for a period varying from 30 minutes to a few hours.

For example, in the case of complexes (IV), the complexing agents of formula (II) according to the invention, in the case when the three chromophores are identical (symmetrical complexing agents) may be prepared from the intermediate (A1):

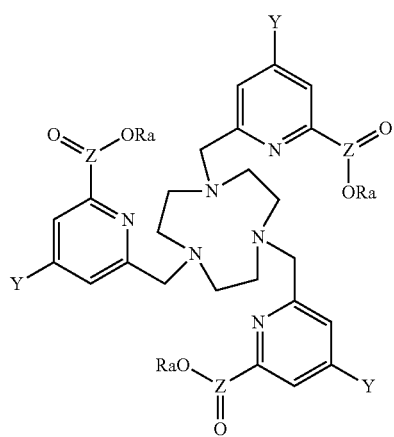

(A1)

wherein Ra is a protective group of acid functions such as an alkyl with 1 to 4 carbon atoms, of the methyl type, Z is as defined for the compounds of formula (IV) and Y which represents a chlorine, bromine and preferably iodine atom, or a function $-N_3$ or $-C\equiv CH$.

The complexing agents of formula (II) according to the invention, in the case when Chrom1=Chrom2≠Chrom3 (dissymmetrical complexing agents) may be prepared from the intermediate (A2):

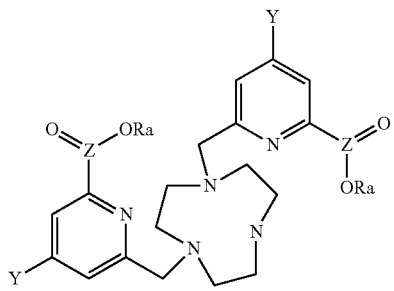

(A2)

wherein Ra is a protective group of acid functions such as an alkyl with 1 to 4 carbon atoms, of the methyl type, Z is as defined for the compounds of formula (IV) and Y which represents a chlorine, bromine, or preferably iodine atom, or a function $-N_3$ or $-C\equiv CH$.

The introduction of groups Chrom1, Chrom2 and Chrom3 may be accomplished in a single step in the case of symmetrical complexing agents from (A1) or in two steps in the case of dissymmetrical complexing agents from (A2) according to techniques detailed in the examples hereafter, or according to similar techniques well known to one skilled in the art.

Within the scope of the invention, the method applying a divergent synthesis from the key intermediates (A1) and (A2) is more rapid and more efficient for preparing complexing agents of formula (IV) than the method proposed for preparing complexing agents in application WO 2013/011236. In the synthesis method used within the scope of the invention, the chromophores Chrom1, Chrom2 and Chrom3 or certain of their precursors are directly introduced on (A1) and (A2) by using standard carbon-carbon coupling reactions catalyzed with palladium, such as the reaction of Sonogashira, of Heck, of Suzuki, of Stille, or further the dipolar 1,3 cycloaddition reactions catalyzed with copper, commonly called «click chemistry».

In every case, the chromophores Chrom1, Chrom2 and Chrom3 will be functionalized with reactive functions compatible with the carbon-carbon or "click chemistry" coupling reactions which are envisioned. These functionalizations are conducted according to procedures from the literature and known to one skilled in the art. Notably the presence of terminal alkyne or alkene functions is notably contemplated in the case of the chromophores Chrom1, Chrom2 and Chrom3 having a spacer, compatible with the Sonogashira and Heck reactions. The presence of a boronic acid function compatible with Suzuki reactions is also contemplated in the case of the chromophores Chrom1, Chrom2 and Chrom3 without any spacer wherein the aryl or heteroaryl group is directly bound to pyridine.

Notably, the introduction of groups:

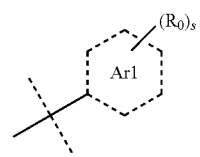

with Ar1, s and $R_0$ (it being understood that various groups $R_0$ may substitute the Ar1 group) which are as defined for the compounds of formula (IV), may be accomplished:

either by action of a compound of formula (V):

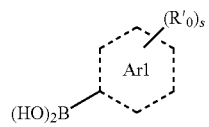

(V)

with R'₀ (it being understood that various groups R'₀ may substitute the Ar1 group) which represents R₀ or a precursor group of R₀ and Ar1, s and R₀ are as defined for the compounds of formula (IV), on the intermediate (A1) or (A2), wherein Y is a chlorine, bromine or preferably iodine atom, under the conditions of Suzuki coupling, or in the case when Ar1 represents a 1,2,3-triazole group, by action of a compound of formula (VI):

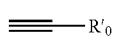

(VI)

with R'₀ which represents R₀ or a precursor group of R₀, R₀ being as defined for the compounds of formula (IV), on the intermediate (A1) or (A2), wherein Y is N₃, by a so-called «click chemistry» reaction. It is also possible to achieve coupling with a compound N₃—R'₀, the alkyne function then being borne by the pyridine of the intermediate (A1) or (A2).

The introduction of groups:

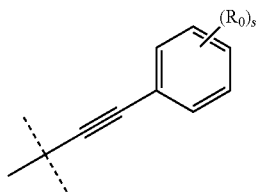

with R₀ (it being understood that various groups R₀ may substitute the phenyl group) as defined for the compounds of formula (IV) may be accomplished by action of a compound of formula (VII):

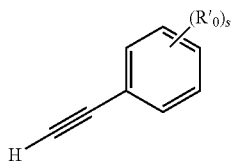

(VII)

with R'₀ (it being understood that various groups R'₀ may substitute the phenyl group) which represents R₀ or a precursor group of R₀, and R₀ and s are as defined for the compounds of formula (IV), on the intermediate (A1) or (A2) wherein Y is a chlorine, bromine or preferably iodine atom, under the conditions of a Sonogashira reaction.

The complexes according to the invention of formula (III) are prepared from a ligand of type (I):

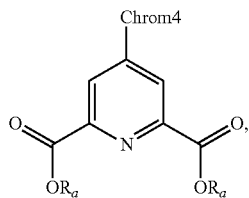

(I)

wherein Chrom4 is as defined earlier for the complexes of formula (III), and Ra is a protective group of acid functions such as an alkyl, for example a methyl.

The complexing agents according to formula (I) are prepared in the same way from intermediates of formula (A3):

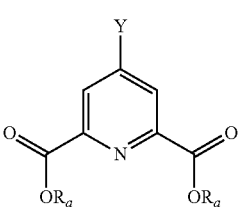

(A3)

wherein Ra is a protective group of acid functions such as an alkyl with 1 to 4 carbon atoms, of the methyl type, and Y represents a chlorine, bromine, or preferably iodine atom, or a function —N₃ or —C≡CH and the synthesis of which is described in A. Picot, C. Feuvrie, C. Barsu, B. Le Guennic, H. Le Bozec, C. Andraud, L. Toupet, O. Maury Tetrahedron. 2008, 64, 399-411 and in Z. El Abidine Chamas, X. Guo, J.-L. Canet, A. Gautier, D. Boyer, R. Mahioub Dalton Trans., 2010, 39, 7091-7097.

Such ligands are prepared according to techniques detailed in the examples hereafter, or according to similar techniques well known to one skilled in the art. In particular, the introduction of groups:

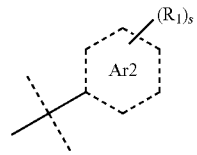

with Ar2, s and R₁ (it being understood that various groups R₁ may substitute the Ar2 group) which are as defined for the compounds of formula (III), may be accomplished:

either by action of a compound of formula (VIII):

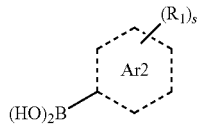

(VIII)

with R'₁ (it being understood that various groups R'₁ may substitute the Ar2 group) which represents R₁ or a precursor group of $R_1$ and Ar2, s and $R_1$ are as defined for the compounds of formula (III), on the compound of formula (IX):

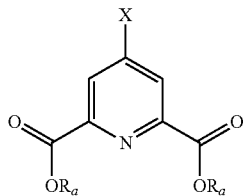

(IX)

with X which is a chlorine, bromine or preferably iodine atom, and Ra which is a protective group of acid functions such as an alkyl, of the methyl type, under the conditions of Suzuki coupling, either in the case when Ar2 represents a 1,2,3-triazole group, by action of a compound of formula:

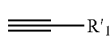

(X)

with $R'_1$ which represents $R_1$ or a precursor group of $R_1$ and $R_1$ which is as defined for the compounds of formula (III), on the compound of formula (XI):

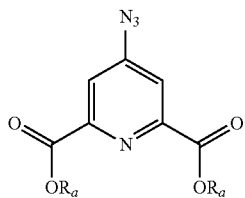

(XI)

with Ra which is a protective group of acid functions such as an alkyl, of the methyl type, by a so-called click chemistry reaction. It is also possible to achieve the coupling with a compound $N_3$—$R'_1$, the alkyne function then being borne by the pyridine of the ligands (I).

The introduction of groups:

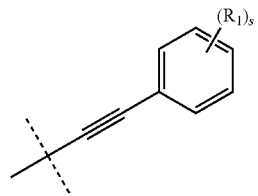

with s and $R_1$ (it being understood that various groups $R_1$ may substitute the phenyl group) as defined for the compounds of formula (III) may be ensured by action of a compound of formula (XII):

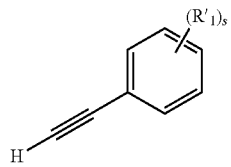

(XII)

with $R'_1$ (it being understood that various groups $R'_1$ may substitute the phenyl group) which represents $R_1$ or a precursor group of $R_1$, and $R_1$ and s are as defined for the compounds of formula (III), on the compound of formula (IX):

(IX)

with X which is a chlorine, bromine or preferably iodine atom and Ra which is a protective group of acid functions such as an alkyl, of the methyl type, under the conditions of a Sonogashira reaction.

Regardless of the contemplated synthesis route and the targeted lanthanide complex, the betaine groups may for example be introduced at the substituents $R_0$ or $R_1$ via direct alkylation of a phenol, thiophenol, aniline group etc. . . . or else via a so called «click chemistry» reaction from a propargyl precursor.

In order to form the corresponding lanthanide complexes, the selected ligand (I) or the macrocycle of formula (II) is put into solution in a solvent in which it is soluble, for example ethanol or methanol, and the de-protection of the acid functions is achieved in a basic medium, and then complexation is conducted with a salt of the desired rare earth, notably as a chloride, triflate or nitrate. Advantageously, about 3 molar equivalents of ligand (I) are used per rare earth atom and about 1 molar equivalent of macrocycle of formula (II) is used per atom of rare earth. The complexation may be achieved at a temperature from 25 to 80° C., for example for a period of the order of 30 minutes to 6 hours.

The examples hereafter allow an illustration of the invention, but do not have any limiting nature.

The acronyms below are used in the examples which follow:
ACN: Acetonitrile
DMF: Dimethylformamide
DPA: Dipicolinic acid
$Et_3N$: Triethylamine
MeOH: Methanol
Ms: A mesyl group
TA: Room temperature
TACN: Triazacyclononane
TBTA: Tris[(1-benzyl-1H-1,2,3-triazol-4-yl)methyl]amine
THF: Tetrahydrofurane
TMSA: Trimethylsilylacetylene
General Information:
The NMR spectra ($^1H$ and $^{13}C$) were recorded on a Bruker AC 200 apparatus at a frequency of 200.13 and 50.32 MHz for $^1H$ and $^{13}C$ respectively and on a Bruker Advance at a frequency of 500.10 and 125.75 MHz for $^1H$ and $^{13}C$ respectively. The chemical shifts (δ) are expressed in parts per million (ppm) relatively to the trimethylsilane used as an internal reference and by using the indicated solvents. The coupling constants (J) are expressed in Hz and the following notations are used: s (singlet), brs (broad singlet), d (doublet), dd (doublet of doublets), m (multiplet).

The high resolution mass spectra HRMS were recorded in the common centre for mass spectrometry at Lyon(s) (Université Claude Bernard Lyon, Lyon, France) on a Micro-TOFQII apparatus equipped with a positive ESI source.

The thin layer chromatographies were carried out on plates of silica gel on aluminium sheets (silica gel, Fluka) and revealed by means of a UV lamp (λ=254 or 365 nm) or by coloration.

The purifications were achieved with a chromatography column on silica gel (silica gel 0.035-0.070 mm, 60 A).

The solvents used for the reactions were purchased from Aldrich or Acros Organics as dry or extra dry solvents and stored on a 3 Å molecular sieve.

The UV/visible absorption spectra were recorded on a JASCO V670 spectrometer; the emission spectra on a JOBIN-YVON fluorolog 3 spectrofluorimeter.

A. PREPARATION OF THE COMPLEXES

Example 1: Europium Complex of Formula (IV)

Scheme 1: Synthesis of the intermediates 3 and 6

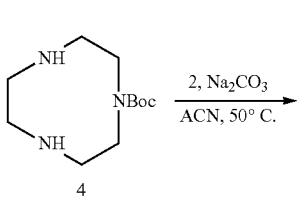
1

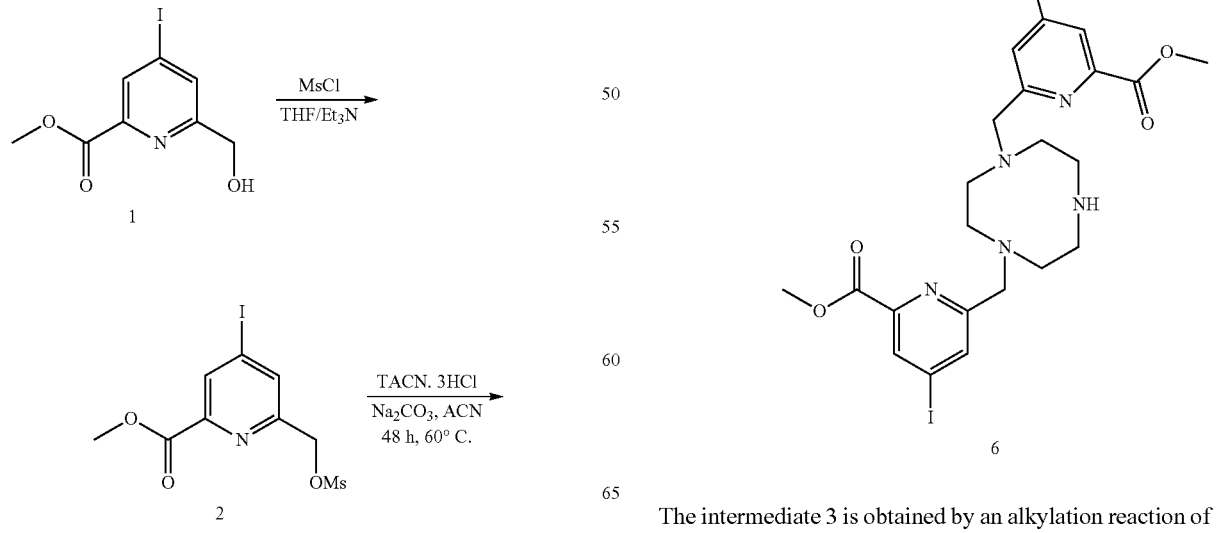

-continued

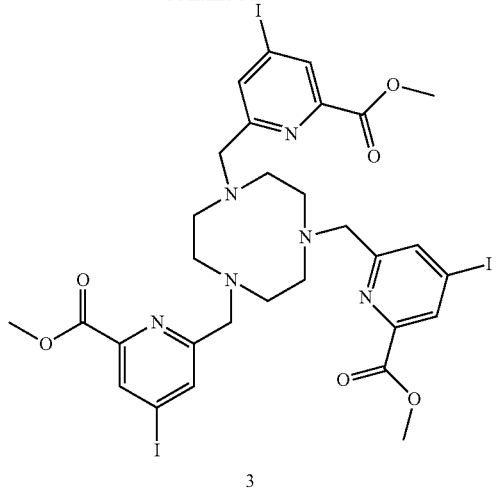
3

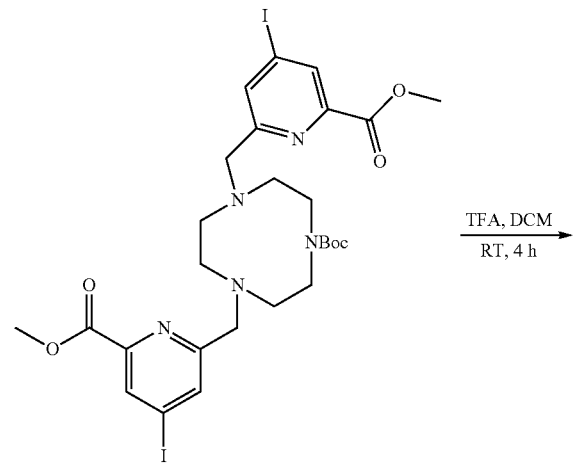

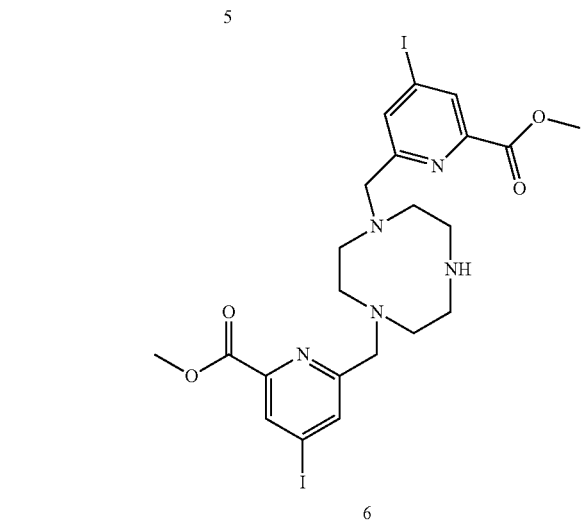
6

The intermediate 3 is obtained by an alkylation reaction of TACN.3HCl, from a mesylate (or tosylate) derivative under standard alkylation conditions. This compound will then be able to be engaged into various crossed coupling reactions in order to obtain the desired ligands.

The synthesis of the dissymmetrical intermediate 6 requires several steps for protection/de-protection of TACN and is prepared according to the method described in patent WO 2013/011236.

TACN-boc 4 is substituted with the compound 2 in order to lead to the compound 5, a precursor of the dissymmetrical intermediate 6 after de-protection of the Boc function.

Scheme 2: Synthesis of europium complexes

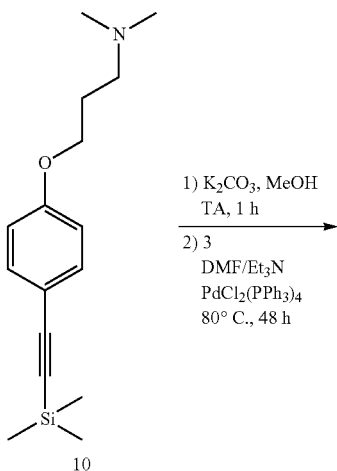

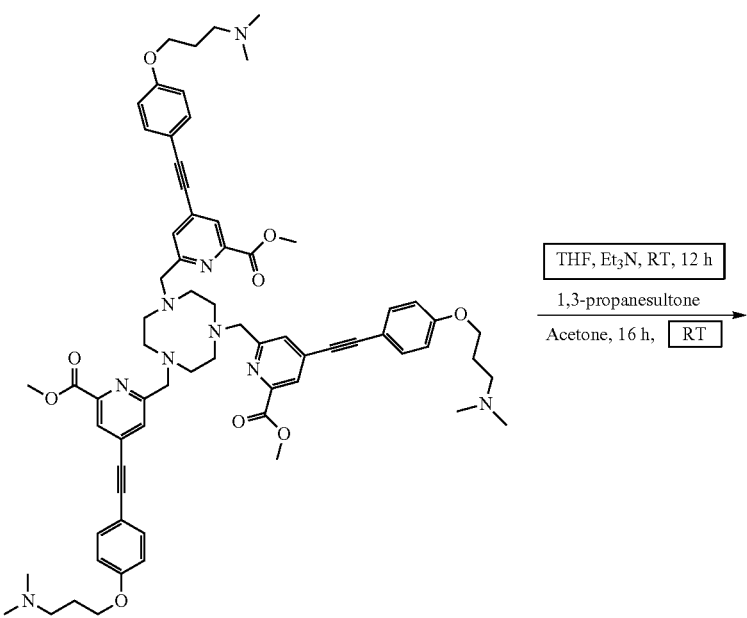

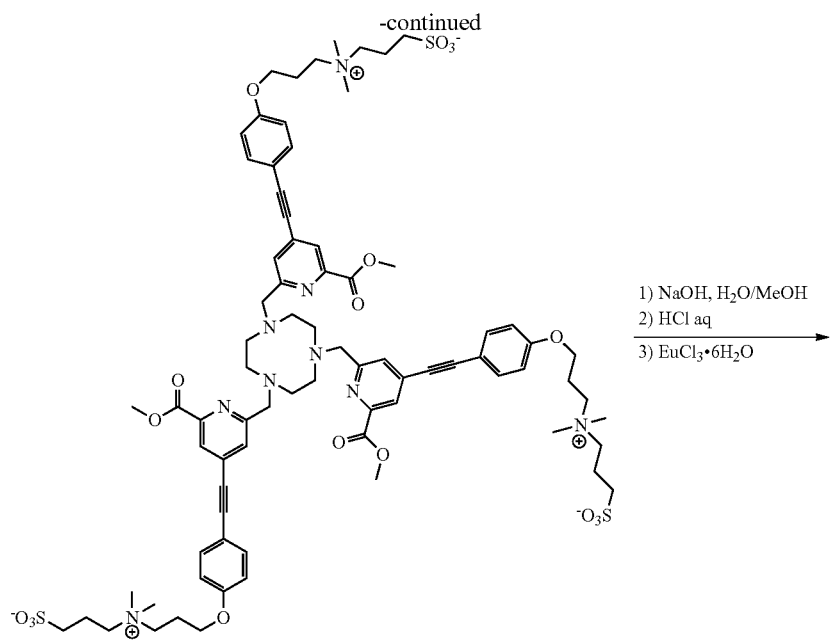

12

1) NaOH, H₂O/MeOH
2) HCl aq
3) EuCl₃·6H₂O

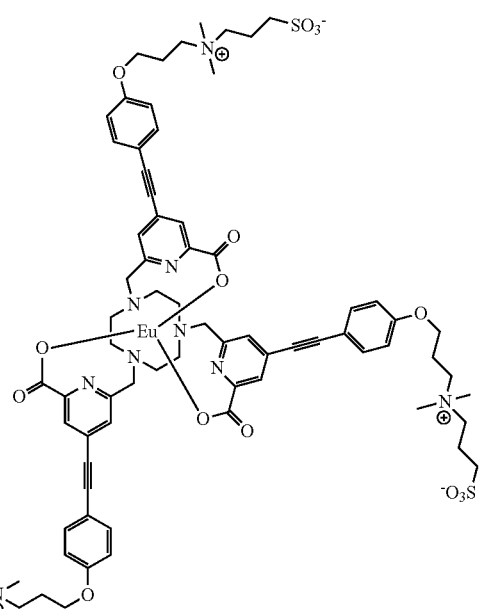

13, Eu2

The synthesis of compound 10 may be achieved under standard substitution conditions on 4-iodophenol from a commercial amine 8. The protected alkyne function of the compound 10 may be introduced via a Sonogashira crossed coupling reaction in the presence of TMSA. The introduction of the compound 10 on the intermediate 3 may be achieved after de-protection of the alkyne, into a real alkyne, which is then directly engaged into a modified Sonogashira coupling step (without CuI). The betaine function may be prepared by a reaction for opening 1,3-propanesultone selectively on the terminal amine of the compound 11 in order to lead to the complexing agent 12. The methyl esters may then be hydrolyzed and the obtained complexing agent reacts in situ in the presence of a europium salt solution in order to lead to the complex Eu2.

Scheme 3: Dissymmetrical synthesis of Eu(III) complexes:
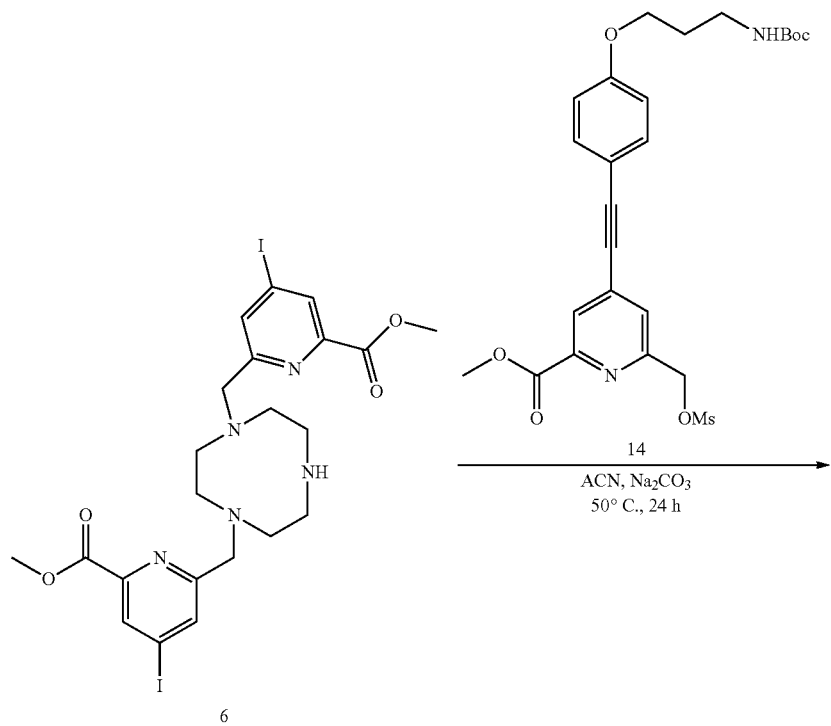
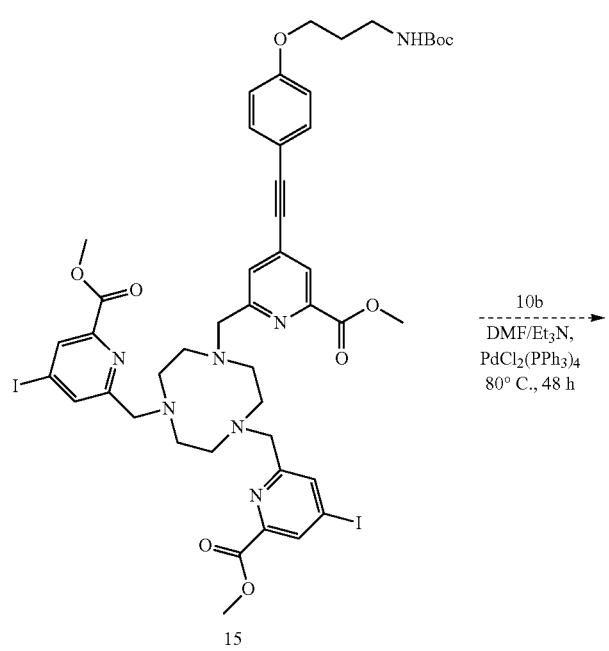

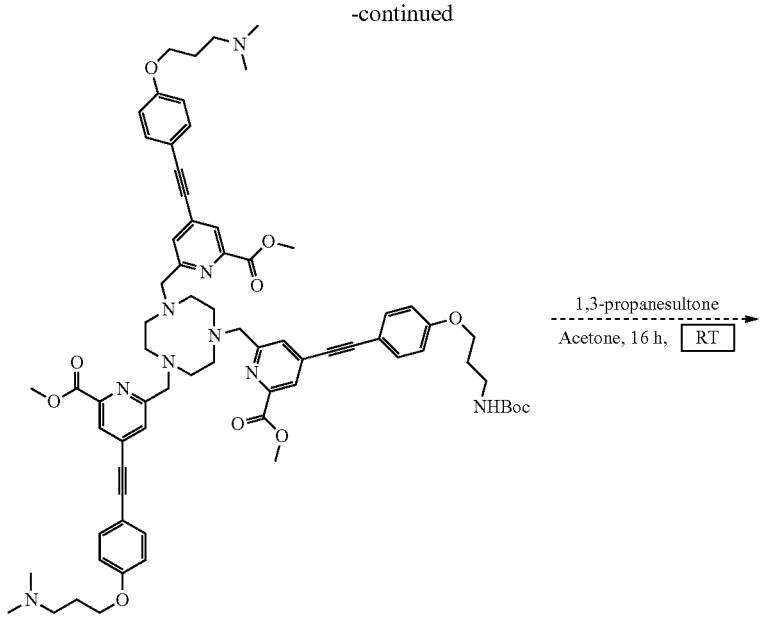
16
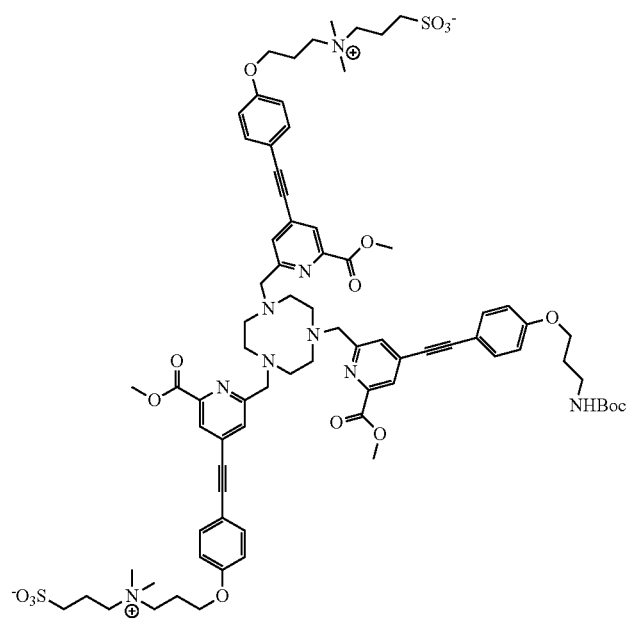
17

The compound 15 is obtained after substituting the compound 6 with the antenna 14. The compound 14 is obtained as described in patent application WO 2013/011236. The compound 16 may be obtained after Sonogashira coupling of the antenna 10b, as described earlier for the symmetrical complex. Also, the compound 17 may be obtained after opening the 1,3-propanesultone selectively on the terminal amines of compound 16.

a) Preparation of Compound 2

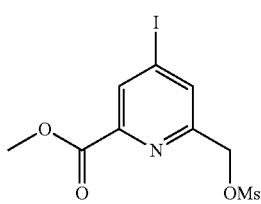

2

The compound 1 (1.56 g, 5.33 mmol, 1.0 equiv.) is dissolved in 50 ml of distilled THF. Triethylamine (1.63 mg, 16 mmol, 3.0 equiv.) is then added, as well as mesyl chloride (976 mg, 8.53 mmol, 1.6 equiv.). The solution is stirred under argon at room temperature. The reaction is tracked by TLC. After 4 h, the reaction is complete, the solvents are evaporated. The residue is solubilized in ethyl acetate and the organic phase is washed with a saturated $NaHCO_3$ solution, and then with water. The organic phase is then dried on $Na_2SO_4$, and then filtered. The solvent is removed under reduced pressure. The obtained raw product is purified by a chromatography column on silica gel (Eluent: dichloromethane/methanol from 0% to 5% by volume, with increments of 1%) leading to the desired product as a white solid (1.40 g, 90%).

$^1$H NMR (500 MHz, $CDCl_3$) δ: 8.47 (d, $^4J$=1.5 Hz, 1H), 8.05 (d, $^4J$=1.5 Hz, 1H), 5.37 (s, 2H), 4.00 (s, 3H), 3.16 (s, 3H)

$^{13}$C NMR (500 MHz, $CDCl_3$) δ: 164, 155, 148, 134, 107, 70, 53, 38

HRMS (ESI$^+$): (Calculated for $C_9H_{10}NO_5SNa$: 393.9212); measured: [M+Na]$^+$: m/z=393.9217.

b) Preparation of Compound 3

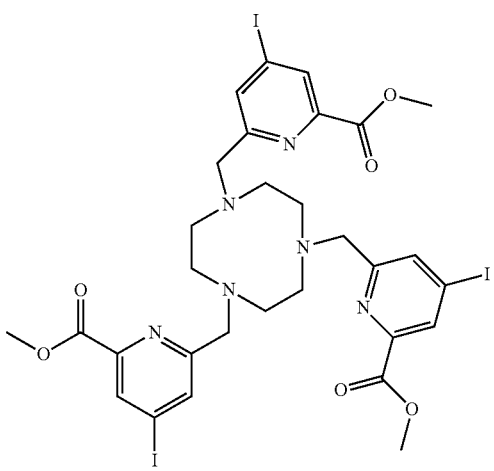

3

To a suspension of $Na_2CO_3$ (1.59 g, 15 mmol, 10 equiv.) in 60 ml of acetonitrile under argon are added TACN.3HCl (356 mg, 1.5 mmol, 1.0 equiv.), and compound 2 (1.4 g, 4.79 mmol, 3.2 equiv.). The reaction mixture is stirred for 48 h at 60° C. under argon. After returning to room temperature, the reaction mixture is filtered and the filtrate is evaporated under reduced pressure. The reaction crude is purified by chromatography on a column of neutral alumina (Eluent: ethyl acetate). The final product is obtained as a yellow solid (814 mg, 57%).

$^1$H NMR (200 MHz, $CDCl_3$) δ: 8.35 (d, J=1.4 Hz, 3H), 8.21 (d, J=1.4 Hz, 3H), 3.97 (s, 9H), 3.93 (s, 6H), 2.90 (s, 12H)

$^{13}$C NMR (125.76 MHz, $CDCl_3$) δ: 164.6, 161.9, 147.65, 147.62, 135.6, 132.8, 106.65, 106.60, 63.9, 56.1, 53.2, 53.19, 53.14.

HRMS (ESI$^+$): (Calculated for $C_{30}H_{34}I_3N_6O_6$: 954.9627); measured: [MH]$^+$: m/z=954.9668.

c) Preparation of Compound 5

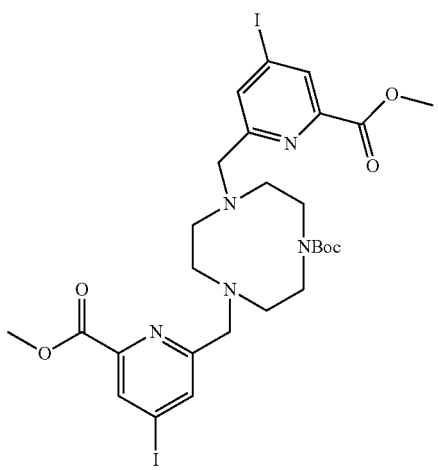

5

In a flask, the compound 4 (370 mg, 1.24 mmol, 1.0 equiv.) is solubilized in dry acetonitrile (100 ml). To this solution are added under argon $Na_2CO_3$ (789 mg, 7.44 mmol, 6.0 equiv.) and the compound 3 (966 mg, 2.6 mmol, 2.1 equiv.). The reaction mixture is stirred under argon at 60° C. for 4 h. At the end of the reaction, the $Na_2CO_3$ is filtered under reduced pressure and the solvents are evaporated. The reaction crude is purified on a chromatography column on silica gel (Eluent: AcOEt). The product is obtained as a yellow oil (633 mg, 66%).

$^1$H NMR (500 MHz, $CDCl_3$) δ: 8.35 (2s, 2H), 8.24 (s, 1H), 8.13 (s, 1H), 3.98 (2s, 2×3H), 3.95 (2s, 2×1H), 3.42 (brs, 2H), 3.36 (brs, 2H), 3.10 (brs, 2H), 2.98 (brs, 2H), 2.7 (brs, 2H), 2.62 (brs, 2H), 1.48 (s, 9H).

$^{13}$C NMR (125.76 MHz, $CDCl_3$) δ: 164.80, 164.73, 162.32, 162.13, 155.79, 147.95, 147.77, 135.57, 135.39, 132.96, 132.92, 106.81, 106.76, 79.69, 63.30, 63.03, 56.77, 55.15, 55.10, 54.59, 53.28, 50.94, 50.42, 28.91.

d) Preparation of Compound 6

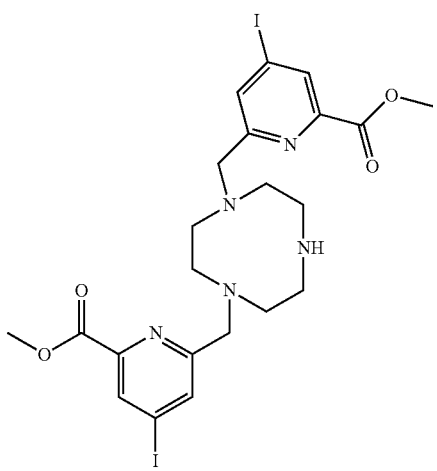

6

In a flask, the compound 5 (50 mg, 6.41·10$^{-2}$ mmol, 1.0 equiv.) is solubilized in CH$_2$Cl$_2$ (2 ml). To this solution is added trifluoroacetic acid (20 equiv.). The reaction mixture is stirred under argon for 4 h. At the end of the reaction, the solvents are evaporated under reduced pressure. The product is obtained as a yellow oil and is directly engaged into the next step without any other purification.

$^1$H NMR (500 MHz, CDCl$_3$) δ: 8.29 (s, 2H), 7.88 (s, 2H), 4.34 (brs, 4H), 3.89 (s, 6H), 3.65 (brs, 4H), 3.51 (brs, 4H), 3.29 (brs, 4H).

e) Preparation of Compound 9

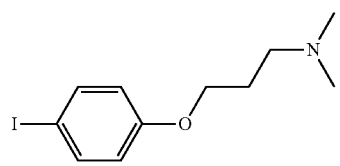

9

In a flask, the compound 7 (1.00 g, 4.54 mmol, 1.0 equiv.) is solubilized in anhydrous DMF (30 mL). To this solution are added the amine 8 (1.07 g, 6.81 mmol, 1.5 equiv.) and K$_2$CO$_3$ (6.30 g, 45.4 mmol, 10 equiv.). The reaction mixture is stirred under argon at 80° C. for 12 h. After returning to room temperature, CH$_2$Cl$_2$ is added. The organic phase is washed three times with an aqueous saturated NaCl solution, and then with water, dried on Na$_2$SO$_4$, filtered and evaporated. The product is obtained as a yellow powder without any other purification (1.20 g, 87%).

$^1$H NMR (200 MHz, CDCl$_3$) δ: 7.54 (d, 2H, J=8.9 Hz), 6.73 (d, 2H, J=8.9 Hz), 3.97 (t, 2H, J=6.4 Hz), 2.43 (t, 2H, J=6.9 Hz), 2.25 (s, 6H), 1.93 (m, 2H).

$^{13}$C NMR (50.32 MHz, CDCl$_3$) δ: 159.04, 138.26, 117.07, 82.65, 66.47, 56.43, 45.67, 27.60.

HRMS (ESI$^+$): (Calculated for C$_{11}$H$_{16}$INO: 305.0277); measured: [MH]$^+$: m/z=306.0349 f) Preparation of Compound 10

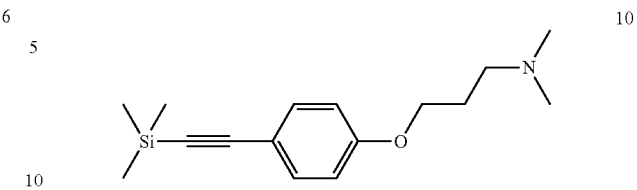

10

In a Schlenk tube, the compound 9 (860 mg, 2.81 mmol, 1.0 equiv.) is solubilized in a THF/Et$_3$N mixture (20 ml, 1/1, v/v). The solution is degassed under argon for 20 min and then TMSA (555 mg, 5.64 mmol, 2.0 equiv.) is added, as well as the catalysts, PdCl$_2$(PPh$_3$)$_2$ (59 mg, 7.86·10$^{-5}$ mol, 0.03 equiv.) and CuI (50 mg, 2.64·10$^{-4}$ mol, 0.1 equiv.). The reaction mixture is stirred under argon at room temperature for 16 h. At the end of the reaction, the solvents are evaporated under reduced pressure. The reaction crude is dissolved in CH$_2$Cl$_2$ and the organic phase is washed with an aqueous solution saturated with NH$_4$Cl, and then with water. The organic phase is then dried on Na$_2$SO$_4$, filtered and evaporated under reduced pressure. The obtained crude product is purified on a chromatography column on silica gel. Eluent CH$_2$Cl$_2$/MeOH (from 0 to 5% by volume). The desired compound is obtained as an orange oil (650 mg, 84%).

$^1$H NMR (200 MHz, CDCl$_3$) δ: 7.36 (d, 2H, J=8.9 Hz), 6.78 (d, 2H, J=8.9 Hz), 3.97 (t, 2H, J=6.4 Hz), 2.43 (t, 2H, J=7.3 Hz), 2.24 (s, 6H), 1.93 (m, 2H), 0.22 (s, 9H).

$^{13}$C NMR (50.32 MHz, CDCl$_3$) δ: 159.33, 133.54, 115.21, 115.21, 114.46, 105.42, 92.39, 66.32, 56.42, 45.66, 27.61.

HRMS (ESI$^+$): (Calculated for C$_{16}$H$_{25}$NOSi: 275.1705); measured: [MH]$^+$: m/z=276.1805 g) Preparation of Compound 10b

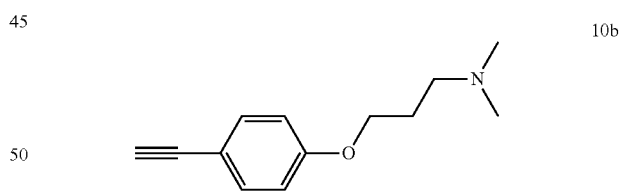

10b

In a flask, the compound 10 (445 mg, 1.61 mmol, 1.0 equiv.) is solubilized in anhydrous MeOH (15 ml). To this solution is added K$_2$CO$_3$ (268 mg, 1.93 mmol, 1.2 equiv.). The reaction mixture is stirred at room temperature for one hour. At the end of the reaction, the solvent is evaporated under reduced pressure. The residue is solubilized in CH$_2$Cl$_2$ and the organic phase is washed twice with water, and then dried on Na$_2$SO$_4$, filtered and evaporated under reduced pressure. The compound is obtained as a brown oil and is directly engaged into the next step without any other purification.

$^1$H NMR (200 MHz, CDCl$_3$) δ: 7.36 (d, 2H, J=8.9 Hz), 6.84 (d, 2H, J=8.9 Hz), 4.02 (t, 2H, J=6.5 Hz), 2.99 (s, 1H), 2.44 (t, 2H, J=7.0 Hz), 2.25 (s, 6H), 1.95 (m, 2H).

h) Preparation of Compound 11

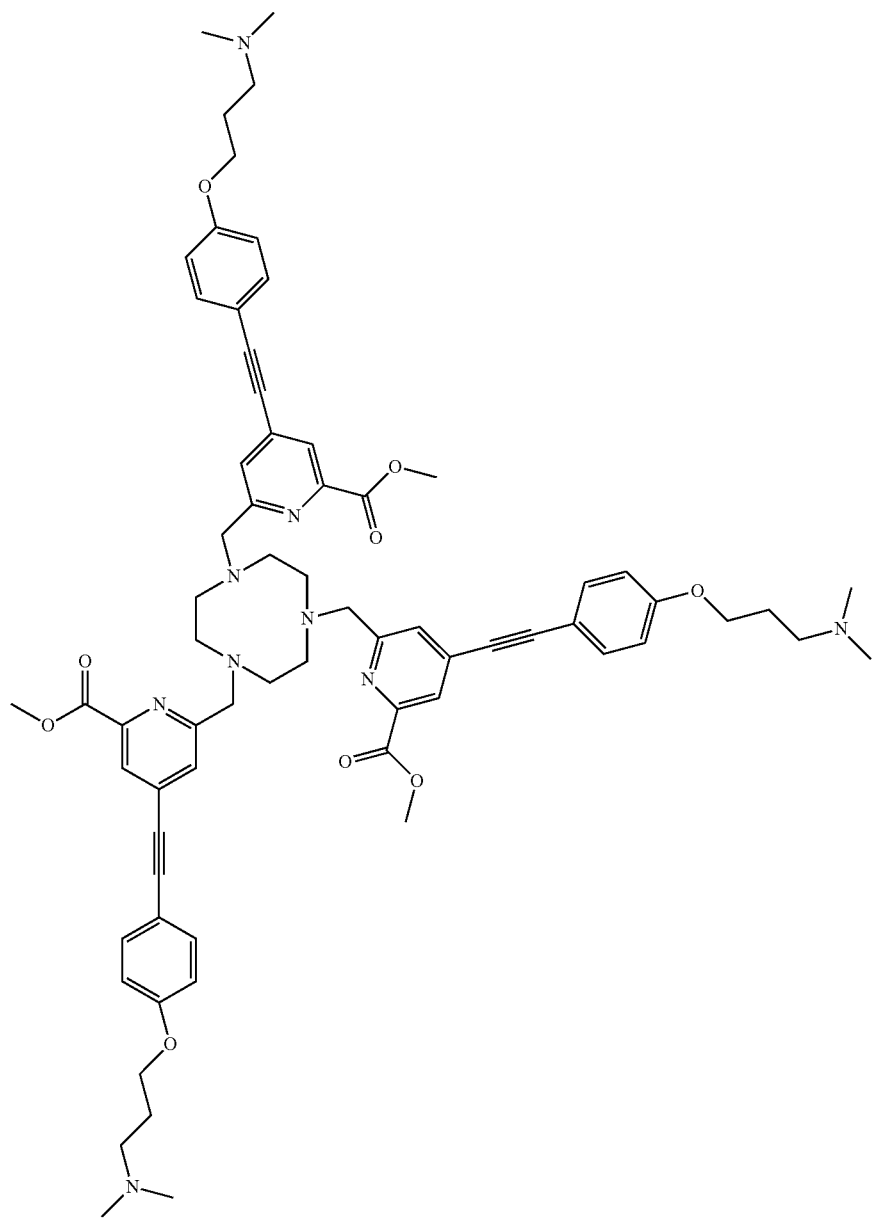

In a Schlenk tube, the derivative 3 (64 mg, 6.76·10$^{-5}$ mol, 1.0 equiv.) is solubilized in a DMF/Et$_3$N mixture (2 ml, 1/1, v/v). The solution is degassed under argon for 30 min. To this solution are then added a solution of 10b (55 mg, 2.70·10$^{-4}$ mol, 4.0 equiv.) solubilized in DMF (1 ml) degassed beforehand under argon, and then PdCl$_2$(PPh$_3$)$_2$ (4 mg, 5.68·10$^{-6}$ mmol, 0.03 equiv.). The reaction mixture is stirred under argon for 48 h at 80° C. At the end of the reaction, the solvents are evaporated under reduced pressure. CH$_2$Cl$_2$ is added to the reaction crude and the organic phase is washed with a saturated Na$_2$CO$_3$ solution, and then with water. The organic phase is then dried on Na$_2$SO$_4$, filtered and then evaporated under reduced pressure. The reaction crude is purified by successive precipitations in an AcOEt/pentane mixture in order to lead to the desired compound as an orange oil (52 mg, 65%).

$^1$H NMR (500 MHz, CDCl$_3$) δ: 8.03 (s, 3H), 7.85 (s, 3H), 7.45 (d, 6H, J=8.8 Hz), 6.88 (d, 6H, J=8.8 Hz), 4.03 (t, 6H, J=6.2 Hz), 3.96 (m, 15H), 2.96 (brs, 12H), 2.45 (t, 6H, J=6.4 Hz), 2.26 (s, 18H), 1.97 (m, 6H).

$^{13}$C NMR (125.76 MHz, CDCl$_3$) δ: 165.73, 161.57, 160.12, 147.47, 133.76, 133.60, 128.74, 127.95, 125.60, 114.87, 113.93, 95.56, 85.65, 66.47, 64.47, 56.40, 56.16, 53.13, 45.59, 45.41, 27.49.

HRMS (ESI$^+$): (Calculated for C$_{69}$H$_{84}$N$_9$O$_9$: 394.2142); measured: [M+3H]$^{3+}$: m/z=394.2125 i) Preparation of Compound 12:

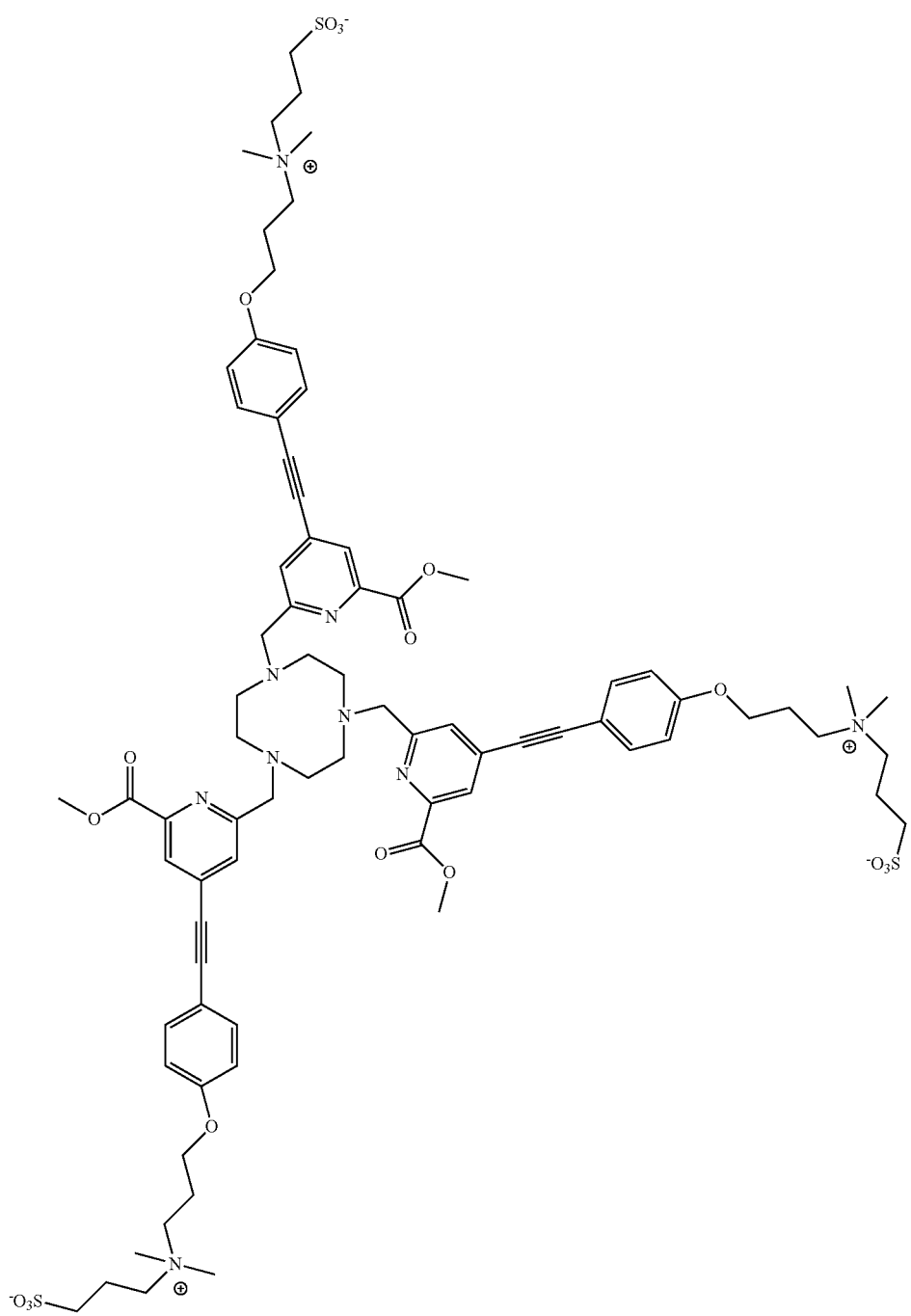

12

The compound 11 (36 mg, 3.05·10⁻⁵ mol, 1.0 equiv.) is solubilized in 1 ml of acetone. 1,3-propanesultone is added and the reaction mixture is stirred under argon at room temperature for 16 h. At the end of the reaction, the solvent is evaporated and the residue is triturated in CH$_2$Cl$_2$. The product is obtained as an orange oil (40 mg, 85%).

$^1$H NMR (200 MHz, CDCl$_3$) δ: 7.83 (s, 3H), 7.67 (s, 3H), 7.38 (d, 6H, J=8.9 Hz), 6.93 (d, 6H, J=8.9 Hz), 4.26 (brs, 4H), 4.16-4.10 (m, 8H), 3.92 (s, 9H), 3.69-3.48 (m, 16H), 3.17 (brs, 12H), 2.94-2.90 (m, 6H), 2.37-2.13 (m, 6H)

j) Preparation of the Complex 13, Eu2

The compound 12 (25 mg, 1.65·10⁻⁵ mol, 1.0 equiv.) is solubilized in a MeOH/H$_2$O mixture (4 ml, 1/1, v/v). To this solution is added an aqueous NaOH solution (1M) (4 ml) and the reaction mixture is stirred under argon for one hour. At the end of the reaction an aqueous solution of HCl is added down to a pH=2. To this mixture are then added a solution of Na$_2$CO$_3$ (8.0 equiv.) as well as the salt EuCl$_3$.6H$_2$O (3.0 equiv.). The reaction mixture is stirred under argon at 50° C. for 16 h. At the end of the reaction, the solvents are evaporated under reduced pressure and the complex is purified by dialysis in H$_2$O for 24 h. The product is obtained as a white powder.

HRMS (ESI$^+$): (Calculated for C$_{75}$H$_{90}$EuN$_9$Na$_4$O$_{18}$S$_3$: 436.3593); measured: [M+4Na]$^{4+}$: m/z=436.3589 k) Preparation of Compound 15

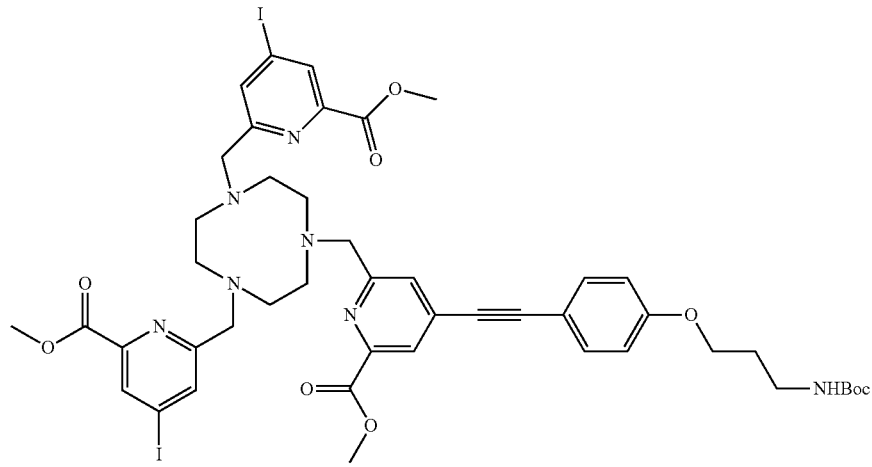

The compound 6 (86 mg, 1.28·10$^{-4}$ mol, 1.0 equiv.) is solubilized in 4 ml of ACN. To this solution is added under argon the compound 14 (86 mg, 1.66·10$^{-4}$ mol, 1.3 equiv.) and Na$_2$CO$_3$ (40 mg, 3.84·10$^{-4}$ mol, 3.0 equiv.). The reaction mixture is stirred under argon at 50° C. for 24 h. At the end of the reaction, the solvents are evaporated and the crude product is purified by chromatography column on Al$_2$O$_3$ (Eluent: CH$_2$Cl$_2$/MeOH from 0 to 5% of MeOH). The product is obtained as a yellow oil (m=60 mg, 42%)

$^1$H NMR (300 MHz, CDCl$_3$) δ: 8.07-8.06 (m, 2H), 7.98 (s, 1H), 7.79 (s, 1H), 7.62 (s, 1H), 7.20 (d, 2H, J=8.5 Hz), 6.62 (d, 2H, J=8.5 Hz), 3.81-3.76 (m, 4H), 3.73-3.64 (m, 13H), 3.09-3.03 (m, 4H), 2.74-2.62 (m, 9H), 1.73 (t, 2H, J=6.37 Hz), 1.17 (s, 9H).

Example 2: The Terbium Complex of Formula (IV)

Scheme 4: Synthesis of terbium complexes 20

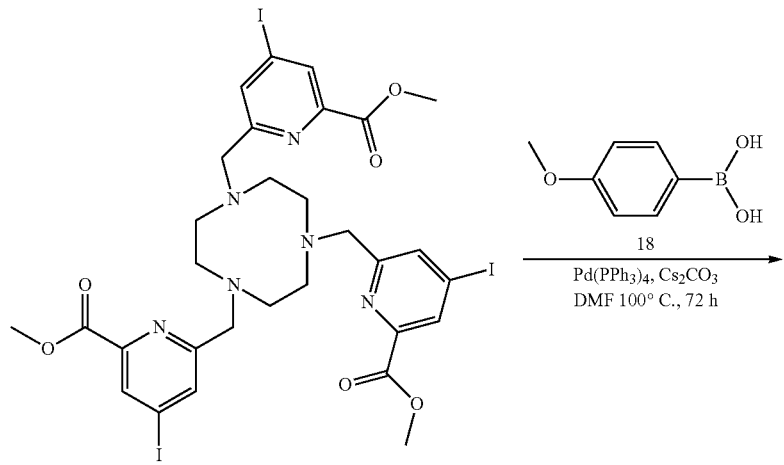

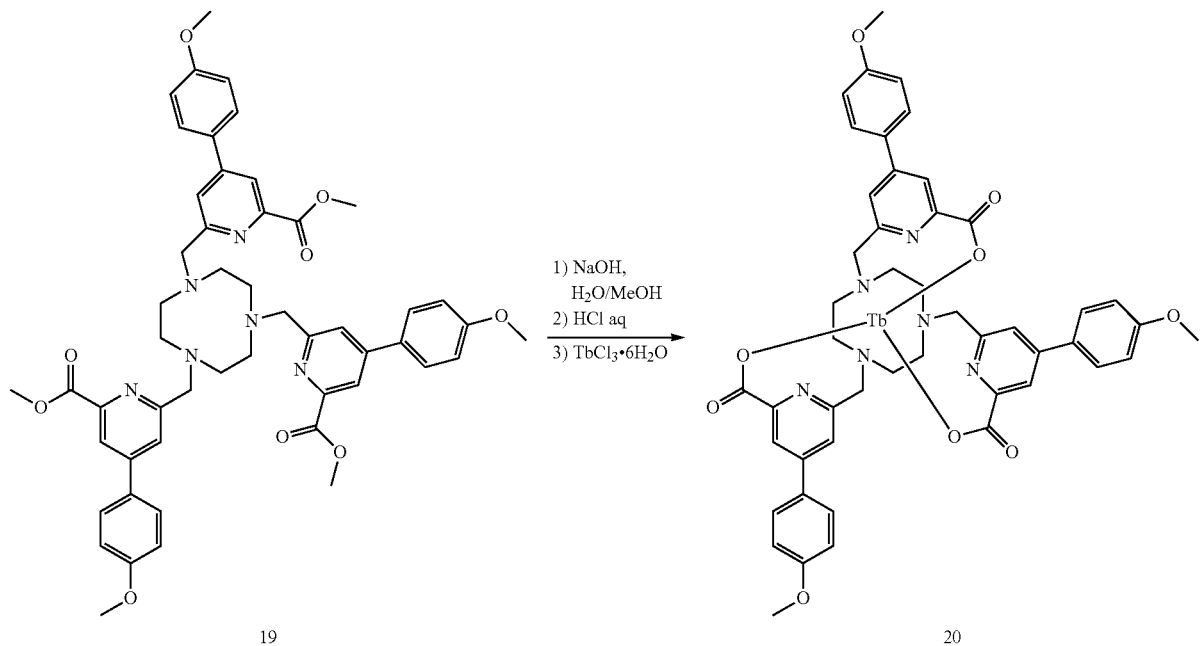
In the same way, the intermediate 3 may react under Suzuki coupling conditions in the presence of boronic acid 18 in order to lead to the ligand 19. The methyl esters are then hydrolyzed in a basic medium and the compound reacts in situ in the presence of Tb(III) salt in order to lead to the formation of the complex 20.
Scheme 5: Synthesis of terbium complexes Tb2
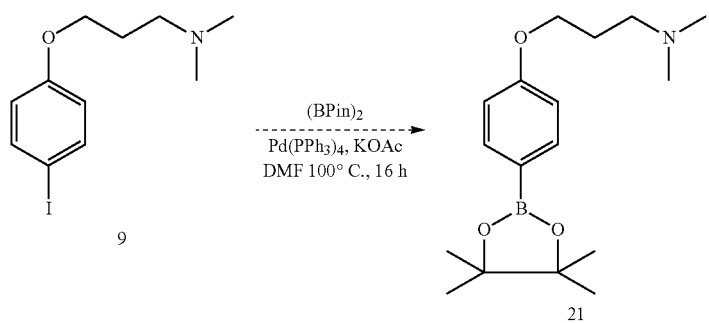

-continued
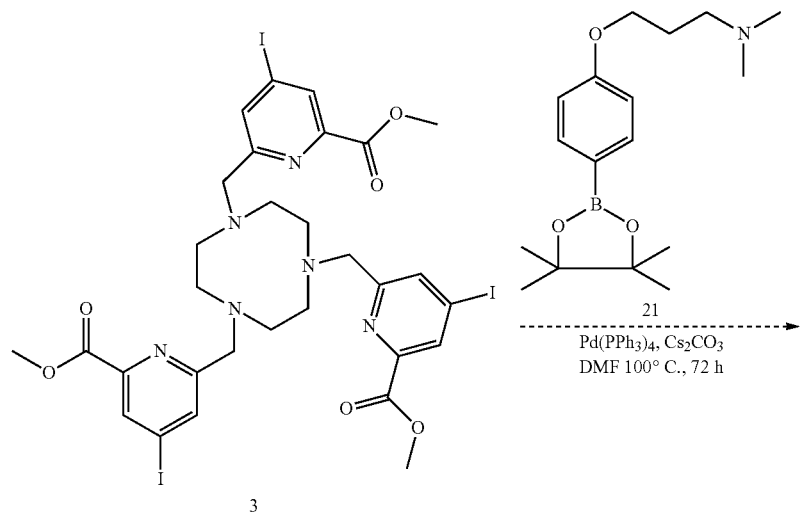
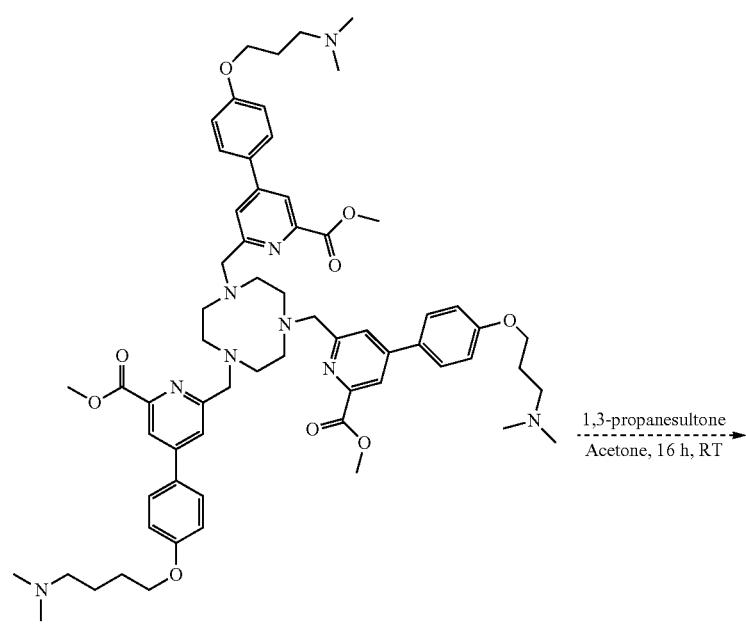

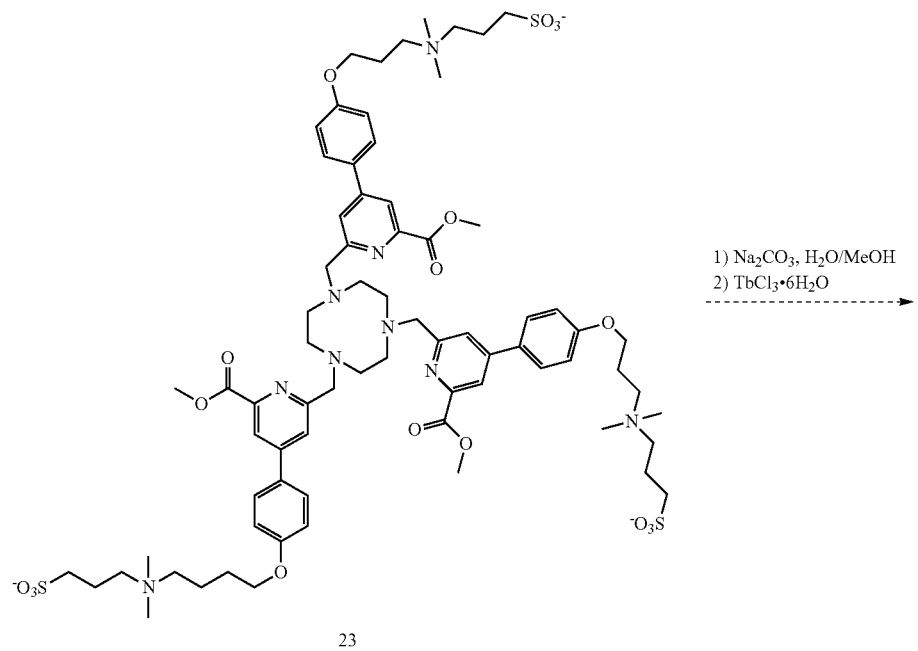
23
1) Na₂CO₃, H₂O/MeOH
2) TbCl₃•6H₂O
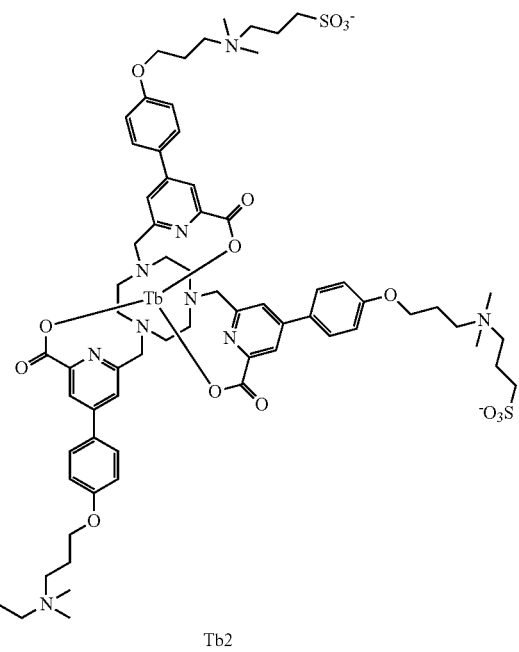
Tb2

The complex Tb2 bearing betaine functions may be obtained via the same synthesis route as its analogue 20. The intermediate 3 may react via a Suzuki reaction with the corresponding antenna 21. The ligand 22 may react in the presence of 1,3-propanesultone in order to lead to the ligand 23. As previously, the complex will be formed in situ in the presence of the corresponding Tb(III) salt in order to lead to the complex Tb2.

a) Preparation of Compound 19:

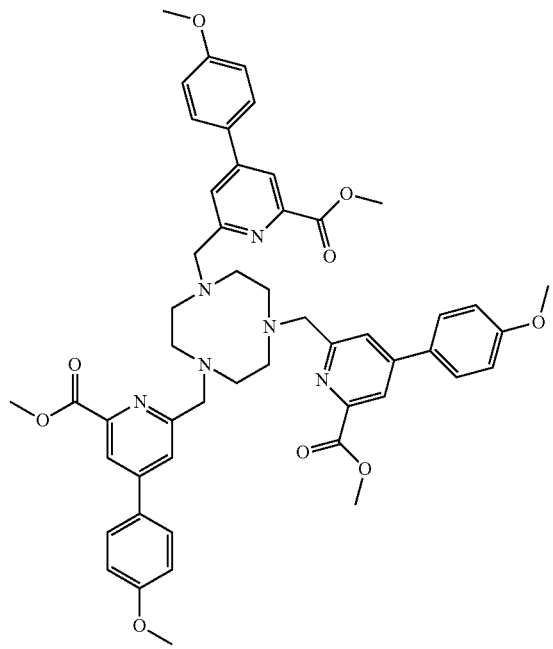

19

In a Schlenk tube, the intermediate 3 (150 mg, $1.57 \cdot 10^{-4}$ mol, 1.0 equiv.) and boronic acid 18 (79 mg, $5.18 \cdot 10^{-4}$ mol, 3.3 equiv.) are solubilized in anhydrous DMF (4 ml). The solution is degassed under argon for 30 min. To this solution are then added $Cs_2CO_3$ (215 mg, $6.59 \cdot 10^{-4}$ mol, 4.2 equiv.) and $Pd(PPh_3)_4$ (10 mg, $9.42 \cdot 10^{-6}$ mmol, 0.06 equiv.). The reaction mixture is stirred under argon for 72 h at 100° C. At the end of the reaction, $Cs_2CO_3$ is filtered under reduced pressure and rinsed several times with $CH_2Cl_2$. The filtrate is evaporated under reduced pressure and diluted in $CH_2Cl_2$. The organic phase is washed with a saturated NaCl solution, and then with water. The organic phase is then dried on $Na_2SO_4$, filtered and then evaporated under reduced pressure. The reaction crude product is purified by successive precipitations from an AcOEt/pentane mixture in order to lead to the desired compound as an orange oil (58 mg, 41%).

$^1$H NMR (200 MHz, $CDCl_3$) δ: 8.19 (s, 3H), 8.02 (s, 3H), 7.58 (d, 6H, J=8.8 Hz), 6.94 (d, 6H, J=8.9 Hz), 4.02 (s, 6H), 3.99 (s, 9H), 3.85 (s, 9H), 3.02 (brs, 12H).

$^{13}$C NMR (50.32 MHz, $CDCl_3$) δ: 166.33, 161.79, 161.03, 149.37, 147.95, 129.60, 128.35, 123.33, 121.21, 114.81, 65.05, 56.48, 55.59, 29.90.

HRMS ($ESI^+$): (Calculated for $C_{51}H_{55}N_6O_9$: 895.4032); measured: $[MH]^+$: m/z=895.4025.

b) Preparation of the Complex Tb2

The Tb2 complex is prepared in a similar way to the complex Eu2, by using the procedure described in Example 1, paragraph f).

HRMS ($ESI^+$): (Calculated for $C_{48}H_{45}N_6Na_2O_9Tb$: 527.1144); measured: $[M+2Na]^{2+}$: m/z=527.1143

Example 3: Terbium Complex of Formula (III)

Scheme 6: Synthesis of Tb complexes with DPA ligands

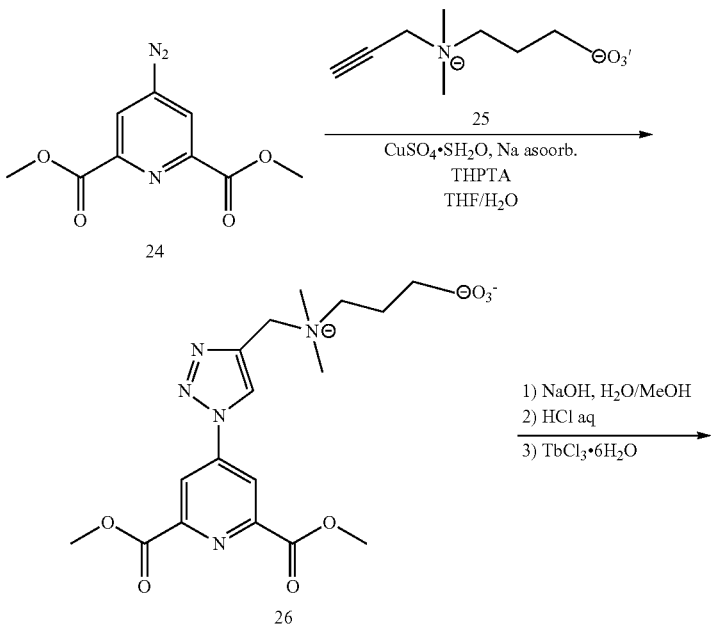

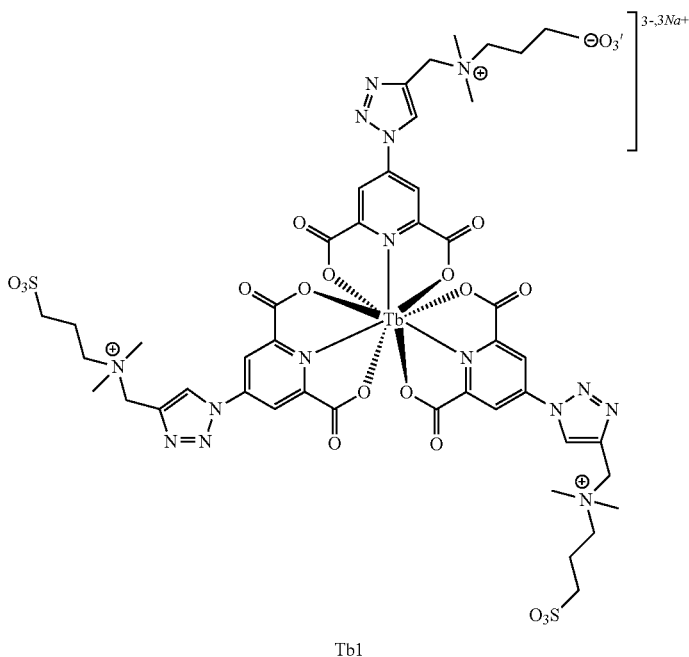

Tb1

In the case of complexes of DPA derivatives, the introduction of betaine groups may be achieved via two different synthesis routes. The betaine group may be introduced in a single "click chemistry" step, as illustrated in Scheme 6, in the case of precursors 24 and 25 for leading to the ligand 26. The methyl esters are then hydrolyzed in a basic medium and the intermediate reacts in the presence of Tb(III) salts for leading to the complex Tb1.

a) Preparation of Compound 26

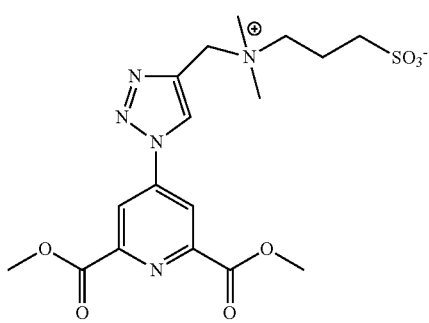

26

The derivative 24 (300 mg, 1.27 mmol, 1.0 equiv.) and the compound 25 (315 mg, 1.52 mmol, 1.2 equiv.) are solubilized in THF (5 ml). To this solution is added a freshly prepared solution of a mixture of $CuSO_4.5H_2O$ (6.5 mg, 0.02 mmol, 0.02 equiv.), of TBTA (15 mg, 0.07 mmol, 0.06 equiv.) and of sodium ascorbate (14 mg, 0.02 mmol, 0.02 equiv.) in a $THF/H_2O$ mixture. The reaction mixture is stirred for 16 h at room temperature. The solvents are then evaporated and the crude product is triturated in acetone. The formed precipitate is filtered under reduced pressure and the desired product is obtained as a white powder (400 mg, 72%).

$^1H$ NMR (500 MHz, $D_2O$) δ: 9.20 (s, 1H), 8.82 (s, 2H), 4.83 (s, 2H), 4.03 (s, 6H), 3.53-3.50 (m, 2H), 3.18 (s, 6H), 2.97 (t, 2H, J=6.8 Hz), 2.38-2.34 (m, 2H).

$^{13}C$ NMR (125.76 MHz, $D_2O$) δ: 166.09, 150.81, 146.44, 137.82, 128.60, 120.08, 63.40, 58.78, 54.89, 51.64, 48.35, 19.49.

HRMS (ESI$^+$): (Calculated for $C_{17}H_{24}N_5O_7S$: 442.1318); measured: [M]$^+$: m/z=442.1391; [M-H+Na]$^+$: m/z=464.1214.

b) Preparation of the Complex Tb1

The complex Tb1 is prepared in a similar way to the complex Eu2, by using the procedure described in Example 1, paragraph f), in the presence of 3.0 equivalents of ligand 18.

Example 4: Europium Complex of Formula (IV)
Scheme 7: Synthesis of complex Eu1
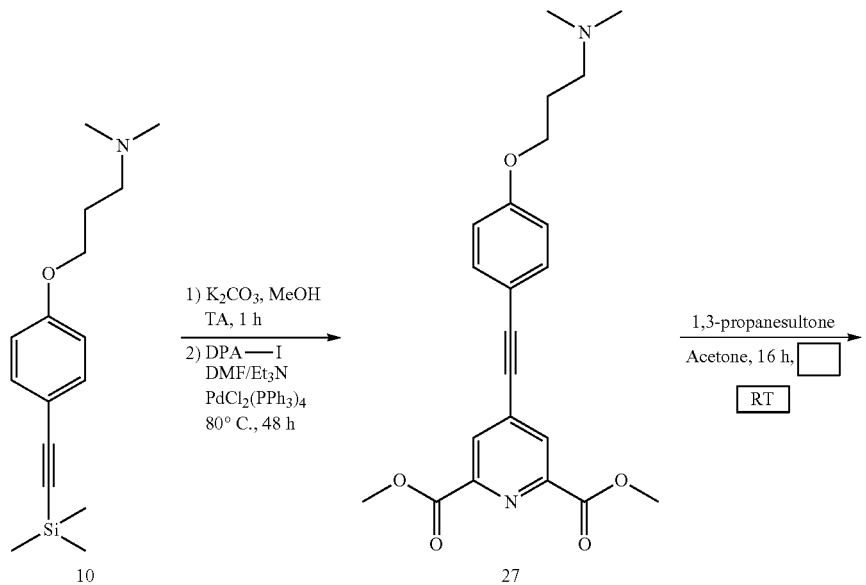
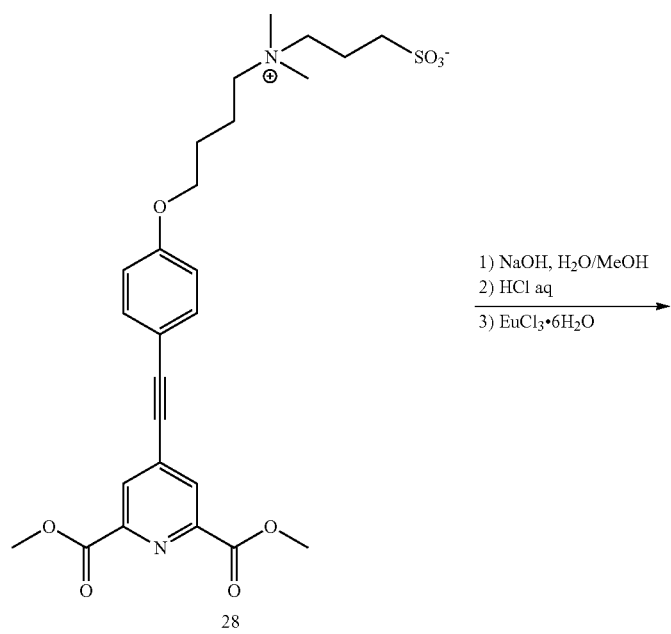

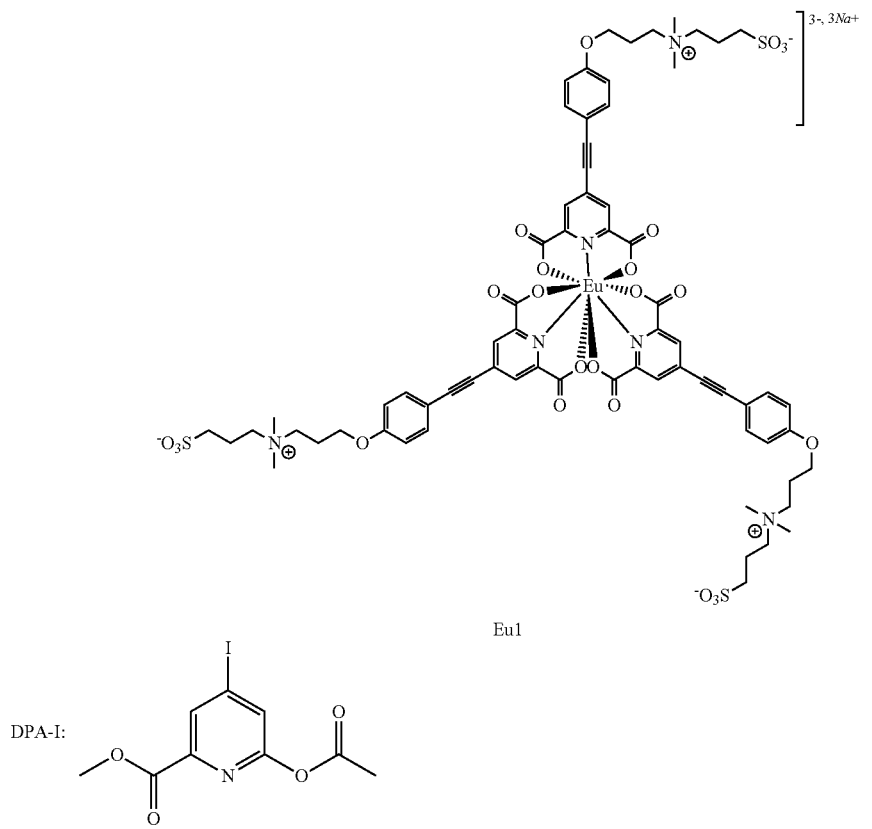

Eu1

DPA-I:

[structure of DPA-I]

The precursor 27 may be obtained via a Sonogashira reaction on the compound DPA-I. The betaine function is in this case introduced by opening the 1,3-propanesultone on the terminal dimethylamine. The methyl esters of the intermediate 28 may then be hydrolyzed in a basic medium and the formed intermediate reacts in the presence of a Eu(III) salt in order to lead to the complex Eu1.

a) Preparation of Compound 27

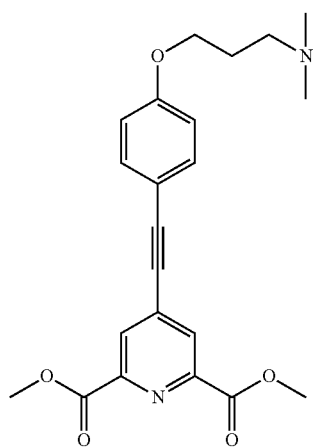

27

In a Schlenk tube, the compound DPA-I (215 mg, $6.72 \cdot 10^{-4}$ mol, 1.0 equiv.) is solubilized in a THF/Et$_3$N mixture (7 ml, 1/1, v/v). The solution is degassed under argon for 20 min and then the compound 10b (265 mg, 1.30 mmol, 1.2 equiv.) is added, as well as the catalysts, PdCl$_2$(PPh$_3$)$_2$ (5 mg, $2.0 \cdot 10^{-5}$ mol, 0.03 equiv.) and CuI (5 g, $6.72 \cdot 10^{-4}$ mol, 0.1 equiv.). The reaction mixture is stirred under argon at room temperature for 16 h. At the end of the reaction, the solvents are evaporated. The reaction crude product is dissolved in CH$_2$Cl$_2$ and the organic phase is washed with an aqueous saturated NH$_4$Cl solution, and then with water. The organic phase is then dried on Na$_2$SO$_4$, filtered and evaporated under reduced pressure. The obtained crude is purified by a chromatography column on silica gel. Eluent CH$_2$Cl$_2$/MeOH (from 0 to 5%). The desired compound is obtained as a yellow powder (210 mg, 80%).

$^1$H NMR (200 MHz, CDCl$_3$) δ: 8.31 (s, 2H), 7.48 (d, 2H, J=8.9 Hz), 6.90 (d, 2H, J=8.9 Hz), 4.90-3.97 (m, 6+2H), 2.51 (t, 2H, J=HZ), 2.33 (s, 6H), 2.03 (m, 2H).

$^{13}$C NMR (50.32 MHz, CDCl$_3$) δ: 164.81, 16.26, 148.34, 134.92, 133.80, 129.45, 114.80, 113.27, 97.59, 84.61, 66.17, 56.16, 53.31, 45.21, 27.03.

HRMS (ESI$^+$): (Calculated for C$_{22}$H$_{25}$N$_2$O$_5$: 397.1744); measured: [MH]$^+$: m/z=397.1758 b) Preparation of Compound 28:

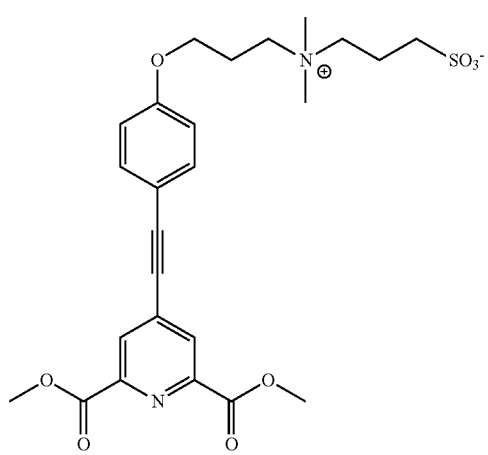

The compound 27 (70 mg, 1.76·10⁻⁴ mol, 1 equiv.) is solubilized in anhydrous acetone. To this solution is added under argon 1,3-propanesultone (22 mg, 1.76·10⁻⁴ mol, 1 equiv.). The reaction mixture is stirred under argon for 2 h. At the end of the reaction, the formed precipitate is filtered under reduced pressure and triturated in an Acetone/$CH_2Cl_2$ mixture (1/1, v/v) and then again filtered. The desired product is obtained as a yellow powder (80 mg, 88%)

$^1$H NMR (500 MHz, MeOD) δ: 8.27 (s, 2H), 7.57 (d, 2H, J=8.9 Hz), 7.01 (d, 2H, J=8.9 Hz), 4.16 (t, 2H, J=6.0 Hz), 4.01 (s, 6H), 3.60-3.57 (m, 4H), 3.17 (s, 6H) 2.89 (t, 2H, J=6.4 Hz), 2.34-2.30 (m, 2H), 2.27-2.23 (m, 2H).

$^{13}$C NMR (125.76 MHz, MeOD) δ: 166.03, 161.40, 149.98, 136.21, 135.16, 130.34, 116.15, 98.18, 85.60, 79.63, 66.03, 63.96, 62.97, 53.65, 30.82, 23.93, 20.06

HRMS (ESI⁺): (Calculated for $C_{25}H_{30}N_2NaO_8S$: 541.1615); measured: [M+Na]⁺: m/z=541.1615 c) Preparation of Complex Tb1:

The Tb1 complex is prepared similarly to the complex Eu2, by using the procedure described in Example 1, paragraph f), in the presence of 3.0 equivalents of ligand 28.

B. EVALUATION OF THE SPECTROSCOPIC PROPERTIES OF THE COMPLEXES a) Spectroscopic Properties of the Complex Eu2 in Water.

The Eu2 complex has good solubility in water of the order of 10⁻⁴-10⁻⁵ mol·L⁻¹), as well as excellent stability in water down to dilutions of the order of 10⁻⁷ mol·L⁻¹. The single FIGURE shows A. the absorption spectrum of the complex Eu2 in water; B. the emission spectrum of the Eu2 complex recorded in water (■$_{excit}$=310 nm).

The complex Eu2 has remarkable spectroscopic properties in water $\lambda_{max}$=335 nm, ε=50,000 L·mol⁻¹·cm⁻¹; Φ=0.18 and τ=0.8 ms, as well as a significant two photon cross-section. Its luminosity at 337 nm is therefore estimated to be 9,000 L·mol⁻¹·cm⁻¹, in the same order of magnitude as its homologues functionalized with PEG fragments described in application WO 2013/011236. These results show that the introduction of betaine functions is not detrimental to the spectroscopic properties of the complex.

In the case of the other synthesized complexes, it is also noticed that by introducing betaine it is possible to improve the solubility of the complexes (as compared with analogue complexes without any betaine) and does not significantly modify the luminescent properties of the complex.

C. STUDY IN A CELL MEDIUM

The compound Eu2 allowed images to be made of bound cells by single or double photon microscopy. Cancer cells T24 (bladder cancer cell line ATCC, HTB-4, see A. Picot, A. D'Aléo, P. L. Baldeck, A. Grichine, A. Duperray, C. Andraud, O. Maury *J. Am. Hem. Soc.* 2008, 130, 1532), were sent with methanol and put into the presence of a solution of the complex (final concentration in the medium=10⁻⁵ mol·L⁻¹). The images of the cells were recorded on a confocal Zeiss microscope operating under single or double photon conditions.

It was observed that the complex Eu2 reversibly labeled the cell. Indeed, after washing, the complex disappears from the cell clearly indicating that functionalization with betaines does not cause irreversible accumulation in lipophilic tissues, underlying forces observed when the PEG groups are used. This clearly shows that the presence of the three betaine groups gives the possibility of avoiding non-specific interactions with the lipophilic portions of the cell.

The invention claimed is:

1. Lanthanide complexes selected among lanthanide complexes of formula (IV):

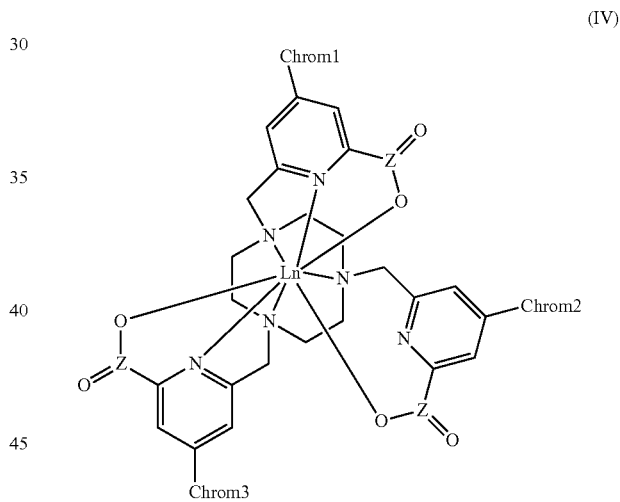

(IV)

wherein:
Ln is a lanthanide, chosen among Eu, Sm, Tb or Dy,
Z represents —C— or —PR₃—,
R₃ represents a phenyl, benzyl, methyl, ethyl, propyl, n-butyl, sec-butyl, iso-butyl or tert-butyl group,
Chrom1, Chrom2 and Chrom3, either identical or different, are selected from the groups:

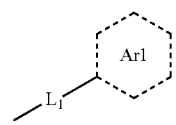

wherein:
L₁ represents a direct bond, —C═C— or —C≡C—,
Ar₁ represents an aromatic group selected among phenyl, thiophenyl, furanyl, pyrrolyl, imidazolyl or triazolyl groups, substituted with s $R_0$ groups, either identical or different, s is equal to 1, 2 or 3, and $R_0$ is selected from:

alkyl groups comprising from 1 to 10 carbon atoms bearing at least one betaine function and/or one reactive function; and electron donor groups selected from O donors, S donors, NHCO donors, SCO donors, NHCS donors, and SCS donors, said electron donor groups may either bear or not bear one or several betaine groups, and/or a reactive function, wherein, when all the groups Ar1 represent a phenyl group, at least one of these phenyl groups is substituted with at least one $R_0$ group including an electron donor group;

wherein at least two of the groups Chrom1, Chrom2 and Chrom3 are substituted with at least one $R_0$ group bearing at least one betaine group.

2. The lanthanide complexes according to claim 1, having, at most, 12 betaine groups.

3. The lanthanide complexes according to claim 1, wherein the at least one reactive function is selected from —COOH, —$NH_2$, an acrylamide, an activated amine, an activated ester, an aldehyde, an alkyl halide, an anhydride, an aniline, an azide, an aziridine, a carboxylic acid, a diazoalkane, a haloacetamide, a halotriazine, a hydrazine, an imido ester, an isocyanate, an isothiocyanate, a maleimide, a sulfonyl halide, a thiol, a ketone, an amine, an acid halide, a hydroxysuccinimidyl ester, a succinimidyl ester, a hydroxysulfosuccinimidyl ester, an azidonitrophenyl, an azidophenyl, a 3-(2-pyridyl-dithio)-propionamide, a glyoxal, a triazine, an acetylene group, and groups of formula:

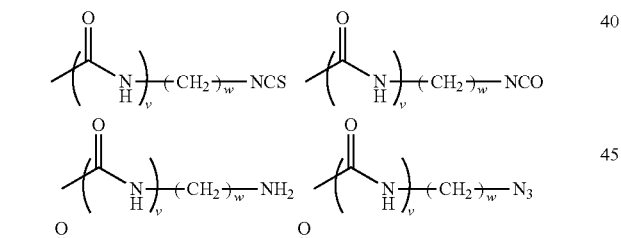

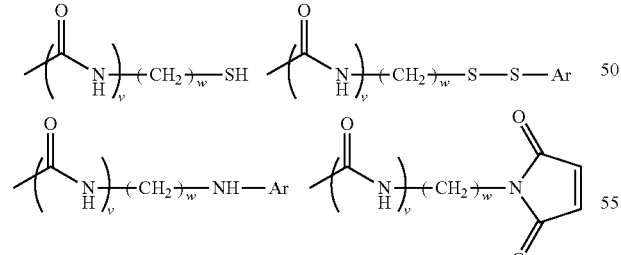

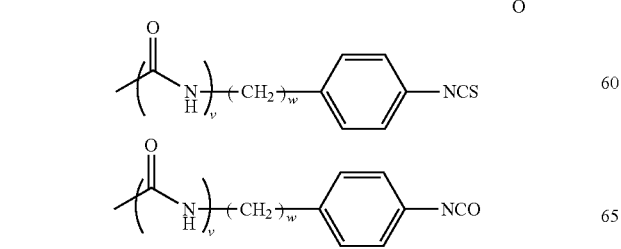

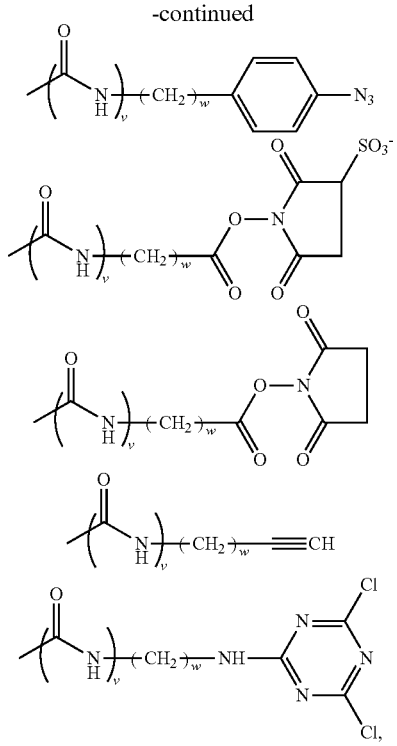

wherein w is an integer belonging to the range from 0 to 8 and v is equal to 0 or 1, and Ar is a saturated or unsaturated heterocycle with 5 or 6 members, comprising from 1 to 3 heteroatoms, optionally substituted with a halogen atom.

4. The lanthanide complexes according to claim 1, wherein Chrom1, Chrom2 and Chrom3 are defined as follows:

a. either Chrom1, Chrom2 and Chrom3, either identical or different, are selected from the groups:

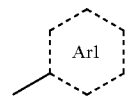

b. or Chrom1, Chrom2 and Chrom3, either identical or different, are selected from the groups:

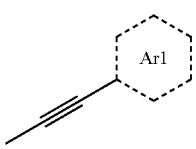 and 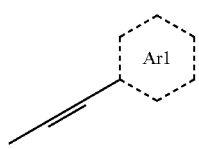

with Ar1 which represents a phenyl, thiophenyl, furanyl, pyrrolyl or imidazolyl group substituted with s $R_0$ groups, either identical or different.

5. The lanthanide complexes according to claim 1, wherein the substituents $R_0$, either identical or different, are selected among:

-$L_2$-Alk, -$L_2$-$L_3$-$Q_1$ and -$L_2$-$L_3$-$Q_2$;

the NHCO donor groups selected among: —NHCO(OAlk), —NHCO(NHAlk), —NHCO(NAlk1Alk2), —NHCO(SAlk), the SCO donor groups selected among: —SCO(OAlk), —SCO(NHAlk), —SCO(NAlk1Alk2), —SCO(SAlk), the NHCS donor groups selected among: —NHCS(OAlk), —NHCS(NHAlk), —NHCS(NAlk1Alk2), and the SCS donor groups selected among: —SCS(OAlk), —SCS(NHAlk), —SCS(NAlk1Alk2), —SCS(SAlk), Alk, Alk1 and Alk2, either identical or different, are alkyl groups comprising from 1 to 10 carbon atoms, optionally substituted with at least one betaine group, $Q_1$ represents a betaine group or a branched group bearing at least two betaine groups, $L_2$ is a direct bond, —O—, —S—, —NHCO—, —SCO—, —NHCS— or —SCS—, $L_3$ is a linker, and $Q_2$ is a reactive group able to allow a covalent bonding with a molecule of interest to be marked, wherein at least two of the present $R_0$ substituents bear at least one betaine group, so that at least two of the groups Chrom1, Chrom2 and Chrom3 are substituted with at least one $R_0$ group bearing at least one betaine group.

6. The lanthanide complexes according to claim 1, wherein Chrom1=Chrom2=Chrom3.

7. The lanthanide complexes according to claim 1, wherein Chrom1=Chrom2 and are substituted with at least one $R_0$ group bearing at least one betaine group and Chrom3 is substituted with at least one $R_0$ group bearing a function -$L_2$-$L_3$-$Q_2$, wherein $Q_2$ represents a group selected among —COOH, —NH$_2$, an acrylamide, an activated amine, an activated ester, an aldehyde, an alkyl halide, an anhydride, an aniline, an azide, an aziridine, a carboxylic acid, a diazoalkane, a haloacetamide, a halotriazine, a hydrazine, an imido ester, an isocyanate, an isothiocyanate, a maleimide, a sulfonyl halide, a thiol, a ketone, an amine, an acid halide, a hydroxysuccinimidyl ester, a succinimidyl ester, a hydroxysulfosuccinimidyl ester, an azidonitrophenyl, an azidophenyl, an 3-(2-pyridyl-dithio)-propionamide, a glyoxal, a triazine, an acetylene group, and the groups of formula:

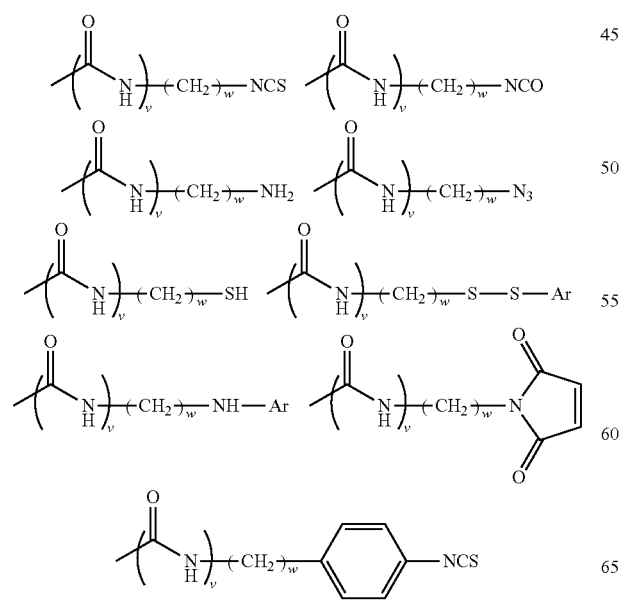

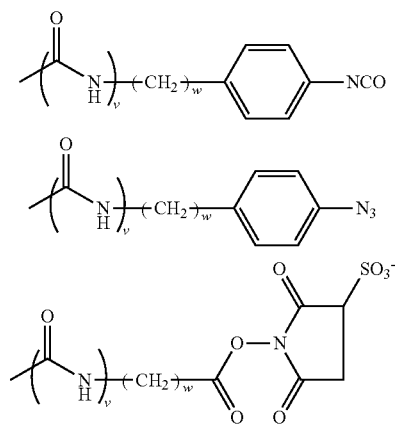

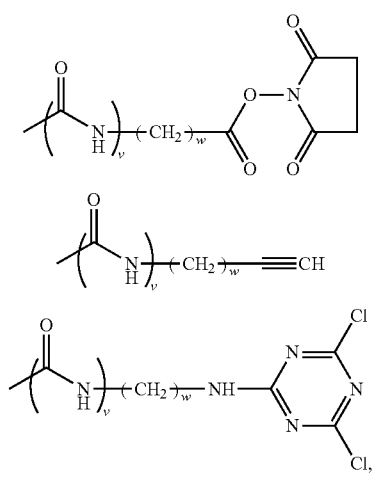

wherein w is an integer belonging to the range from 0 to 8 and v is equal to 0 or 1, and Ar is a saturated or unsaturated heterocycle with 5 or 6 members, comprising 1 to 3 heteroatoms, optionally substituted with a halogen atom.

8. The lanthanide complexes according to claim 1, wherein $L_1$ represents a direct bond or —C≡C—, and the groups Ar1, either identical or different, each represent a phenyl group, substituted with s $R_0$ groups, either identical or different.

9. The lanthanide complexes according to claim 1, wherein, in all the groups Ar1, s is equal to 1.

10. The lanthanide complexes according to claim 1, wherein the groups Ar1, either identical or different, each represent a phenyl group selected from the groups:

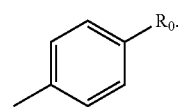

11. The lanthanide complexes according to claim 1, selected among the lanthanide complexes of formula (III):

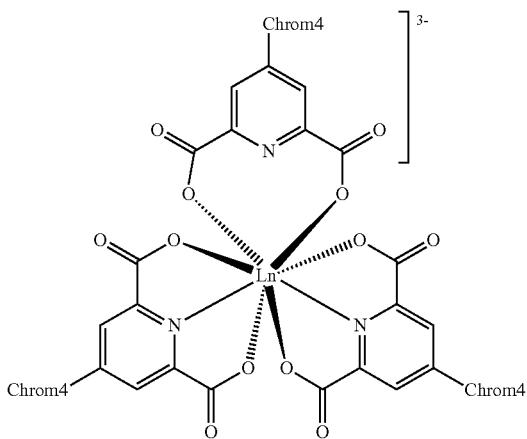
(III)

wherein
Ln is a lanthanide, chosen among Eu, Sm, Tb or Dy,
Chrom4 is selected from the groups:

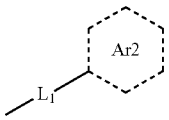

wherein:
$L_1$ represents a direct bond, —C=C— or —C≡C—,
Ar2 represents an aromatic group selected among the phenyl, thiophenyl, furanyl, pyrrolyl, imidazolyl or triazolyl groups, said groups Ar2 being substituted with s $R_1$ groups, either identical or different,
s is equal to 1, 2 or 3, and
$R_1$ is selected among alkyl groups comprising from 1 to 10 carbon atoms bearing at least one betaine group; and electron donor groups selected from O donors, S donors, NHCO donors, SCO donors, NHCS donors, and SCS donors, said electron donor groups bearing one or several betaine groups,
wherein, when the group Ar2 represents a phenyl group, it is substituted with at least one $R_1$ group including an electron donor group.

12. The lanthanide complexes according to claim 11, wherein Ar2 is selected:
a. either from the groups:

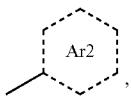, b. or from the groups:

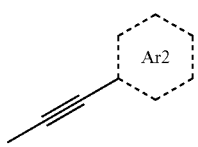 et 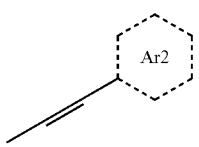

with Ar2 which represents a phenyl, thiophenyl, furanyl, pyrrolyl or imidazolyl group substituted with s $R_1$ groups, either identical or different.

13. The lanthanide complexes according to claim 1, wherein the substituents Ru either identical or different, are selected among:
-$L_2$-Alk, -$L_2$-$L_3$-$Q_1$;
the NHCO donor groups selected among: —NHCO(OAlk), —NHCO(NHAlk), —NHCO(NAlk1Alk2), —NHCO(SAlk),
the SCO donor groups selected among: —SCO(OAlk), —SCO(NHAlk), —SCO(NAlk1Alk2), —SCO(SAlk),
the NHCS donor groups selected among: —NHCS(OAlk), —NHCS(NHAlk), —NHCS(NAlk1Alk2), and
the SCS donor groups selected among: —SCS(OAlk), —SCS(NHAlk), —SCS(NAlk1Alk2), —SCS(SAlk),
Alk, Alk1 and Alk2, either identical or different, are alkyl groups comprising from 1 to 10 carbon atoms, substituted with at least one betaine group,
$Q_1$ represents a betaine group or a branched group bearing at least two betaine groups,
$L_2$ is a direct bond, —O—, —S—, —NHCO—, —SCO—, —NHCS— or —SCS—,
$L_3$ represents a bond arm selected among a covalent bond, an alkylene group from 1 to 12 carbon atoms, optionally comprising one or several double or triple bonds; a cycloalkylene group from 5 to 8 carbon atoms, an arylene group from 6 to 14 carbon atoms; or a sequence of one or several alkylene groups from 1 to 12 carbon atoms, cycloalkylene groups from 5 to 8 carbon atoms and/or arylene groups from 6 to 14 carbon atoms; said alkylene, cycloalkylene or arylene groups may comprise one or several hetero-atoms or not such as oxygen, nitrogen, sulfur, phosphorus atoms or one or several carbamoyl or carboxamido groups and/or may be non-substituted or unsubstituted with one or several alkyl groups from 1 to 8 carbon atoms, aryl groups from 6 to 14 carbon atoms, sulfonate or oxo groups.

14. The lanthanide complexes according to claim 13, wherein $L_3$ is selected from:

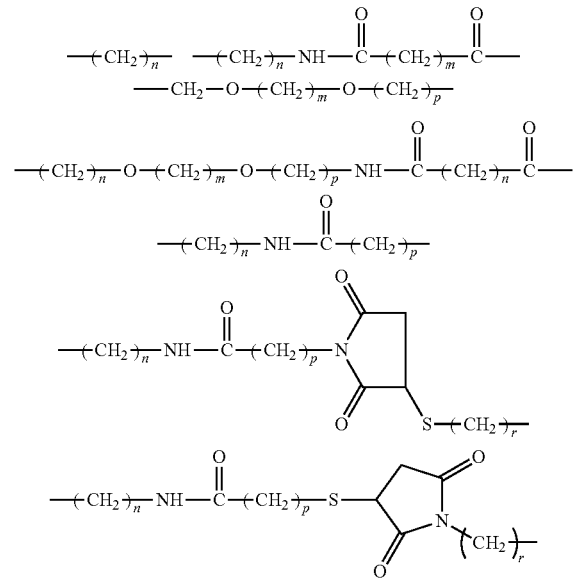

-continued

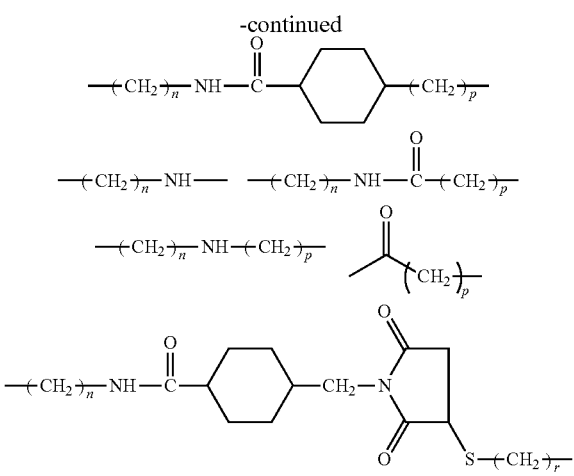

n is equal to 1, 2, 3, 4, 5 or 6,
m, p and r, either identical or different, are equal to 1, 2 or 3.

15. The lanthanide complexes according to claim 1, wherein:
either $Ln^{3+}=Eu^{3+}$ or $Sm^{3+}$ and $L_1$ represents —C≡C—;
or $Ln^{3+}=Eu^{3+}$, $Sm^{3+}$, $Tb^{3+}$ or $Dy^{3+}$, and $L_1$ represents a direct bond.

16. The lanthanide complexes according to claim 1, wherein the betaine groups are selected from zwitterionic groups associating an ammonium or aromatic iminium cation selected among pyridinium, imidazolium cation, and an anionic group selected among sulfonate, phosphonate or carboxylate groups, said cation and said anion being spaced apart by at least one $CH_2$.

17. The lanthanide complexes according to claim 1, wherein the betaine groups are selected among:

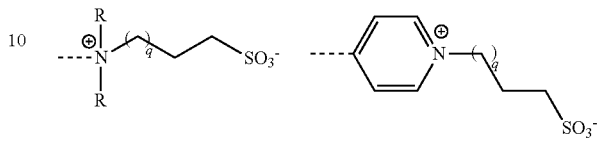

with R which represents an alkyl group from 1 to 6 carbon atoms, and q is equal to 1, 2, 3, 4, 5 or 6.

18. The lanthanide complexes according to claim 1, wherein the reactive function is selected from —COOH, —$NH_2$, succinimidyl esters, haloacetamides, azides, hydrazines, isocyanates, and maleimides.

19. The lanthanide complexes according to claim 1, wherein the betaine group is —$N(CH_3)_2^+$—$(CH_2)_3$—$SO_3^-$.

20. The lanthanide complexes according to claim 7, wherein $Q_2$ is selected among —COOH, —$NH_2$, succinimidyl esters, haloacetamides, hydrazines, isocyanates, and maleimides.

21. The lanthanide complexes according to claim 15, wherein $Ln^{3+}=Tb^{3+}$ or $Dy^{3+}$.

* * * * *